US008383781B2

(12) United States Patent
Wallach et al.

(10) Patent No.: US 8,383,781 B2
(45) Date of Patent: Feb. 26, 2013

(54) ANTI-NIK ANTIBODIES AND USES THEREOF

(75) Inventors: David Wallach, Rehovot (IL); Parameswaran Ramakrishnan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1124 days.

(21) Appl. No.: 10/573,138

(22) PCT Filed: Oct. 5, 2004

(86) PCT No.: PCT/IL2004/000921
§ 371 (c)(1),
(2), (4) Date: Nov. 6, 2006

(87) PCT Pub. No.: WO2005/033142
PCT Pub. Date: Apr. 14, 2005

(65) Prior Publication Data
US 2007/0086994 A1    Apr. 19, 2007

(30) Foreign Application Priority Data
Oct. 7, 2003  (IL) .......................................... 158287

(51) Int. Cl.
C07K 16/40 (2006.01)
C07K 16/46 (2006.01)
A61K 39/395 (2006.01)
C12N 5/20 (2006.01)

(52) U.S. Cl. ........... 530/388.26; 530/388.1; 530/388.15; 530/387.1; 530/387.3; 530/389.1; 424/146.1; 424/141.1; 424/142.1; 424/134.1; 424/130.1; 435/326; 435/346

(58) Field of Classification Search .................. None
See application file for complete search history.

(56) References Cited

U.S. PATENT DOCUMENTS

| 5,030,565 | A | | 7/1991 | Niman et al. |
| 5,854,003 | A | * | 12/1998 | Rothe et al. ................. 435/7.8 |
| 6,822,138 | B1 | * | 11/2004 | Schreiber et al. ............ 800/18 |
| 2003/0082519 | A1 | | 5/2003 | Schubart et al. |

FOREIGN PATENT DOCUMENTS

| WO | WO-90/10231 A1 | 9/1990 |
| WO | WO-95/26365 A1 | 10/1995 |
| WO | WO-97/37016 A1 | 10/1997 |
| WO | WO-03/087380 A1 | 10/2003 |

OTHER PUBLICATIONS

Rudikoff et al Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Lederman et al. Molecular Immunology 28: 1171-1181, 1991.*
Li et al. PNAS 77: 3211-3214, 1980.*
Houghten et al. New Approaches to Immunization, Vaccines 86, Cold Spring Harbor Laboratory, p. 21-25, 1986.*
Chen et al., NIK is a component of the EGF/heregulin receptor signaling complexes. *Oncogene*, 22(28): 4348-55 (2003).
Laune et al., Systematic exploration of the antigen binding activity of synthetic peptides isolated from the variable regions of immunoglobulins. *J. Biol. Chem.*, 272(49): 30937-44 (1997).
International Search Report and Written Opinion of the International Searching Authority, PCT/IL2004/000921, dated Apr. 27, 2005.
International Preliminary Report on Patentability, PCT/IL2004/000921, dated Nov. 25, 2005.

* cited by examiner

*Primary Examiner* — Sharon Wen
(74) *Attorney, Agent, or Firm* — Marshall, Gerstein & Borun LLP

(57) ABSTRACT

An antibody or antibody preparation being capable of specifically binding the amino acid sequence of NF-&kgr;B-inducing kinase (NIK) MAP3K14, or a specific portion thereof, and of thereby regulating a biochemical activity of NIK, and/or enabling detection of NIK or a specific portion thereof.

34 Claims, 9 Drawing Sheets

Figure 2

```
  1  MAVMEMACPG  APGSAVGQQK  ELPKPKEKTP  PLGKKQSSVY  KLEAVEKSPV   50
 51  FCGKWEILND  VITKGTAKEG  SEAGPAAISI  IAQAECENSQ  EFSPTFSERI  100
101  FIAGSKQYSQ  SESLDQIPNN  VAHATEGKMA  RVCWKGKRRS  KARKKRKKKS  150
151  SKSLAHAGVA  LAKPLPRTPE  QESCTIPVQE  DESPLGAPYV  RNTPQFTKPL  200
201  KEPGLGQLCF  KQLGEGLRPA  LPRSELHKLI  SPLQCLNHVW  KLHHPQDGGP  250
251  LPLPTHPFPY  SRLPHPFPFH  PLQPWKPHPL  ESFLGKLACV  DSQKPLPDPH  300
301  LSKLACVDSP  KPLPGPHLEP  SCLSRGAHEK  FSVEEYLVHA  LQGSVSSSQA  350
351  HSLTSLAKTW  AARGSRSREP  SPKTEDNEGV  LLTEKLKPVD  YEYREEVHWA  400
401  THQLRLGRGS  FGEVHRMEDK  QTGFQCAVKK  VRLEVFRAEE  LMACAGLTSP  450
451  RIVPLYGAVR  EGPWVNIFME  LLEGGSLGQL  VKEQGCLPED  RALYYLGQAL  500
501  EGLEYLHSRR  ILHGDVKADN  VLLSSDGSHA  ALCDFGHAVC  LQPDGLGKSL  550
551  LTGDYIPGTE  THMAPEVVLG  RSCDAKVDVW  SSCCMMLHML  NGCHPWTQFF  600
601  RGPLCLKIAS  EPPPVREIPP  SCAPLTAQAI  QEGLRKEPIH  RVSAAELGGK  650
651  VNRALQQVGG  LKSPWRGEYK  EPRHPPPNQA  NYHQTLHAQP  RELSPRAPGP  700
701  RPAEETTGRA  PKLQPPLPPE  PPEPNKSPPL  TLSKEESGMW  EPLPLSSLEP  750
751  APARNPSSPE  RKATVPEQEL  QQLEIELFLN  SLSQPFSLEE  QEQILSCLSI  800
801  DSLSLSDDSE  KNPSKASQSS  RDTLSSGVHS  WSSQAEARSS  SWNMVLARGR  850
851  PTDTPSYFNG  VKVQIQSLNG  EHLHIREFHR  VKVGDIATGI  SSQIPAAAFS  900
901  LVTKDGQPVR  YDMEVPDSGI  DLQCTLAPDG  SFAWSWRVKH  GQLENRP     947
```

Figure 4
Fig. 4a
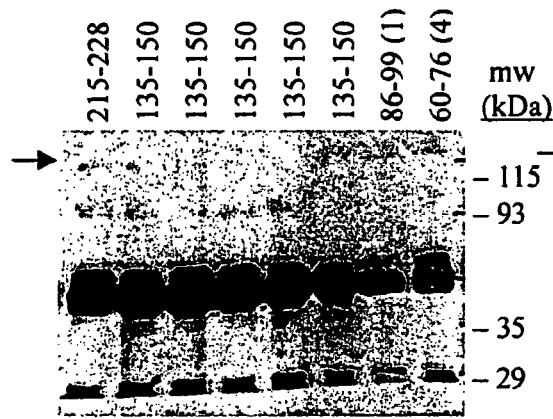
Fig. 4b
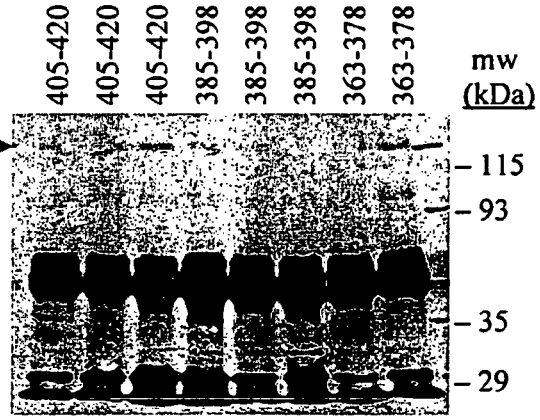
Fig. 4c
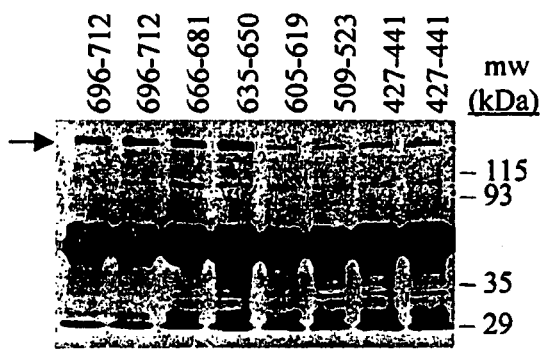
Fig. 4d
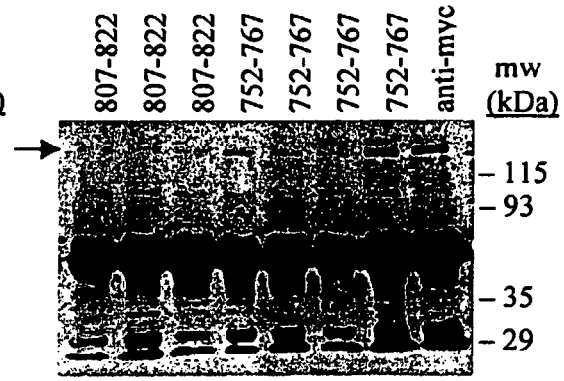

ANTI-NIK ANTIBODIES AND USES THEREOF

This application is a U.S. National Phase application pursuant to 35 U.S.C. §371 of International Application No. PCT/IL2004/000921, which was filed Oct. 5, 2004, claiming benefit of priority of Israeli Patent Application No. 158287, which was filed Oct. 7, 2003. The entire disclosure of each of the foregoing applications is incorporated herein by reference.

FIELD OF THE INVENTION

The present invention relates to immunoregulatory molecules. More particularly, the present invention relates to antibodies or antibody fragments capable of specifically binding NF-κB-inducing kinase (NIK)/MAP3K14, or a specific portion thereof, and of thereby regulating a biochemical activity of NIK, and/or enabling detection of NIK or a specific portion thereof.

BACKGROUND OF THE INVENTION

No treatment or no satisfactory treatment exists for numerous lethal and/or highly debilitating diseases associated with disregulated activity of NF-κB molecules, including malignant diseases and diseases associated with pathological immune responses, such as autoimmune, allergic, inflammatory, and transplantation-related diseases.

NF-κB family molecules are eukaryotic transcription factor complexes critical for the regulation of immune responses, cell growth, and survival (Ghosh S. et al., 1998 Annu Rev Immunol. 16:225-60) which are inducibly activated by almost all TNF/NGF receptor family members. NF-κB molecules are normally sequestered in the cytoplasmic compartment by physical association with a family of cytoplasmic ankyrin-rich inhibitors termed IκB, including IκBα and related proteins (Baldwin A S. Jr., 1996. Annu Rev Immunol. 14:649-83). In response to diverse stimuli, including cytokines, mitogens, and certain viral gene products, IκB is rapidly phosphorylated at Ser32 and Ser36, and is ubiquitinated and subsequently degraded by the 26S proteasome. This allows the liberated NF-κB to translocate to the nucleus and participate in target gene transactivation (Mercurio F. and Manning A. M., 1999. Curr Opin Cell Biol. 11:226-32; Pahl, H. L., 1999. Oncogene 18:6853-66). Recent molecular cloning studies have identified a multi-subunit IκB kinase (IKK) complex that mediates the signal-induced phosphorylation of IκB, the inhibitor of NF-κB. The IKK complex is composed of two catalytic subunits, IKKα and IKKβ, and a regulatory subunit IKKγ (NEMO). The catalytic activity of both IKKα and IKKβ can be activated by a multitude of different NF-κB inducers, including inflammatory cytokines such as tumor necrosis factor (TNF) and interleukin (IL)-1, the T-cell receptor (TCR) and the T-cell costimulatory protein, CD28 (Karin, M. and Ben-Neriah, Y., 2000. Annu Rev Immunol. 18:621-63).

NF-κB-inducing kinase (NIK)/MAP3K-14 (WIPO Pub. No. WO9737016A1 to the present inventors) is critical for activation of NF-κB. For example, overexpression of NIK has been shown to lead to dramatic activation of NF-κB (reviewed in Wallach D. et al., 2002. Arthritis Res. 4 Suppl 3:S189-96), and expression of catalytically-inactive NIK mutants has been shown to lead to effective inhibition of NF-κB activation in response to a variety of known NF-κB activators, such as LMP1, TNF receptor (TNFR)-1, TNFR-2, RANK, human Toll receptor, CD3/CD28, IL-1 receptor (IL-1R), human T-cell lymphotropic virus (HTLV)-1 Tax protein, and lipopolysaccharide (LPS) (Malinin, N. L. et al., 1997. Nature 385:540-4; Sylla, B. S. et al., 1998. Proc Natl Acad Sci USA. 95:10106-11; Darnay, B. G. et al., 1999. J Biol Chem. 274:7724-31; Lin, X. et al., 1999. Immunity 10:271-80; Geleziunas, R. et al., 1998. Mol Cell Biol. 18:5157-65). Targeted disruption of the NIK gene (Yin, L. et al., 2001. Science 291:2162-5), and study of the 'alymphoplasia' (aly) mouse strain bearing a natural Gly855Arg missense point mutation in NIK (Shinkura, R. et al., 1999. Nat Genet. 22:74-7) revealed that NIK has an essential role in lymphoid organ development. Both aly/aly and NIK knockout mice manifest systemic absence of lymph nodes and Peyer's patches, disorganized splenic and thymic architectures, and immunodeficiency whose most resilient features are low serum immunoglobulin levels and lack of graft rejection (Shinkura, R. et al., 1999. Nat Genet. 22:74-7). These abnormalities apparently reflect aberrant signaling by a variety of receptors. The developmental deficiencies of the NIK mutant mice resemble those found in mice deficient in the LT-β receptor (LT-βR) suggesting that NIK also participates in signaling by this particular receptor. Impaired B cell proliferative capacity in the aly/aly mice could be shown to correlate to a deficient response of these cells to LPS and CD40 ligand (CD40L; Garceau, N. et al., 2000. J Exp Med. 191:381-6), and presence of excessive amounts of B1 cells in the peritoneal cavity of mice could be ascribed to defects in homing of peritoneal cells to the gut-associated lymphatic tissue (GALT) system as a consequence of deficient chemokine receptor signaling in secondary lymphoid tissue (Fagarasan, S. et al., 2000. J Exp Med. 191:1477-86).

An important and general role for NIK in cytokine receptor signaling has been recently demonstrated in studies performed by Wallach et al. who have shown, using a two-hybrid system, that the IL-2 receptor γ chain, or "common γ chain" which is a signaling component the receptors for IL-2, -4, -7, IL-9, -13, -15 and -21, specifically associates with NIK (PCT/IL 03/00317). Overexpression of the common γ chain was found to potentiate NF-κB activation mediated by NIK, and upon IL-2 or IL-15 stimulation, NIK and signalosome components were found to bind to common γ chain. These results therefore indicate involvement of NIK in signaling via the large variety of cytokine receptors comprising common γ chain as a signaling subunit.

Apart from these and other contributions to the regulation of the development and function of the immune system, NIK is also involved in the regulation of various non-immune functions. The aly/aly (though not the NIK knockout) mice display deficient mammary gland development (Miyawaki, S. et al., 1994. Eur J Immunol. 24:429-34). Moreover, in-vitro studies have implicated NIK in signaling leading to skeletal muscle cell differentiation (Canicio, J. et al., 2001. J Biol Chem. 276:20228-33), and to survival and differentiation of neurons (Foehr, E. D. et al., 2000. J Biol Chem. 275:34021-4).

Consistent with the suggested role of NIK as mediator of NF-κB activation, fibroblasts derived from aly/aly and NIK knock-out mice fail to activate NF-κB in response to LT-βR activation. Moreover, LT-βR upregulation of VCAM-1, which occurs through NF-κB activation, is abnormal in aly/aly mouse embryonic fibroblasts (MEFs; Matsumoto, M. et al., 1999. J Immunol. 163:1584-91). Deficient phosphorylation of IκB has also been noted in the response of aly/aly B-lymphocytes to CD40 ligation. In contrast, in dendritic cells of these mice, CD40-induced phosphorylation of IκB appeared normal (Garceau, N. et al., 2000. J Exp Med. 191:381-6). Aly/aly peritoneal cells are also incapable of responding to the chemokine SLC with increased NF-κB activity (Fagarasan, S. et al., 2000. J Exp Med. 191:1477-86).

Assessment of the pattern of expressed NF-κB species in lymphoid organs of aly/aly mice indicated that, apart from its role in the regulation of NF-κB complex(es) comprised of Rel proteins (A+p50) and IκB, NIK also participates in controlling the expression/activation of other NF-κB species. Most notably, lymphocytes of aly/aly are deficient for p52, an NF-κB species that is specifically formed in mature B lymphocytes through proteolytic processing of an inactive precursor, p100 (NF-κB2), suggesting a deficiency in p100 to p52 conversion (Yamada, T. et al., 2000. J Immunol. 165:804-12). Indeed, NIK has been shown to participate in site-specific phosphorylation of p100. Both directly lead to phosphorylation of IKKα which in turn phosphorylates p100. This phosphorylation serves as a molecular trigger for ubiquitination and active processing of p100 to form p52. This p100 processing activity was found to be ablated by the aly mutation (Xiao, G. et al., 2001. Mol Cell 7:401-9; Senftleben, U. et al., 2001. Science 293:1495-9).

In view of the structural homology of NIK to MAP3Ks, some attempts have been made to explore the involvement of NIK in the ERK, JNK and p38 cascades, the three other main protein kinase cascades involving MAP3Ks (Akiba, H. et al., 1998. J Biol Chem. 273:13353-8). NIK has been shown to be involved in the ERK cascade in PC12 phaeochromocytoma cells (Foehr, E. D. et al., 2000. J Biol Chem. 275:34021-4). Evidence has also been presented that in certain cells NIK may participate in signaling for phosphorylation of Jun, the downstream target of the JNK cascade, independently of this particular cascade (Akiba, H. et al., 1998. J Biol Chem. 273: 13353-8; Natoli, G. et al., 1997. J Biol Chem. 272:26079-82). Overall, these findings indicate that NIK indeed serves as a mediator of NF-κB activation, but may also serve other functions, and that it exerts these functions in a cell- and receptor-specific manner.

Similarly to other MAP3Ks, NIK can be activated as a consequence of phosphorylation of the 'activation loop' within the NIK molecule. Indeed, mutation of a phosphorylation-site within this loop (Thr559) prevents activation of NF-κB upon NIK overexpression (Lin, X. et al., 1999. Immunity 10:271-80). In addition, the activity of NIK seems to be regulated through the ability of the regions upstream and downstream of its kinase motif to bind to each other (Lin et al. Molec. Cell Biol. (18) 10 5899-5907 1998). The C-terminal region of NIK downstream of its kinase moiety has been shown to be capable of binding directly to IKKα (Regnier, C. H. et al., 1997. Cell 90:373-83) as well as to p100 (Xiao, G. and Sun, S. C., 2000. J Biol Chem. 275:21081-5) and to TRAF2 (Malinin, N. L. et al., 1997. Nature 385:540-4). Such interactions are apparently required for NIK function in NF-κB signaling. The N-terminal region of NIK contains a negative-regulatory domain (NRD), which is composed of a basic motif (BR) and a proline-rich repeat motif (PRR) (Xiao, G. et al., 2001. Mol Cell 7:401-9). Apparently, the N-terminal NRD interacts with the C-terminal region of NIK in cis, thereby inhibiting the binding of NIK to its substrate (IKKα and p100). Ectopically expressed NIK seems to spontaneously form oligomers in which these bindings of the N-terminal to the C-terminal regions in each NIK molecule are apparently disrupted, and display a high level of constitutive activity (Lin, X. et al., 1999. Immunity 10:271-80). The binding of the NIK C-terminal region to the TNF-receptor-associated adaptor protein TRAF2, as well as to other TRAFs, (Malinin, N. L. et al., 1997. Nature 385:540-4; Rothe, M. et al., 1994. Cell 78:681-92; Takeuchi, M. et al., 1996. J Biol Chem. 271:19935-42) most likely participates in the activation of NF-κB by NIK.

Evidence has been presented that NIK, through the binding of its C-terminal region to IKKα, can activate the IKK complex. It has been shown to be capable of phosphorylating Ser176 in the activation loop of IKKα and to thereby activate this molecule (Ling, L. et al, 1998. Proc Natl Acad Sci USA. 95:3792-7). Consistently with such a mode of action, studies regarding the mechanisms accounting for the deficiency in NF-κB activation by LT-βR in aly/aly MEFs have indicated that the NIK mutation ablates activation of the IKK signalosome and the consequent phosphorylation of IκB (Matsushima, A. et al, 2001. J Exp Med. 193:631-6). The ability of NIK to bind p100 directly through its C-terminal region and phosphorylate it suggests that p100 serves as a direct NIK substrate (Xiao, G. and Sun, S. C., 2000. J Biol Chem. 275: 21081-5). Nevertheless, a recent study has suggested that NIK mediates p100 phosphorylation in an indirect way, through phosphorylation and thus activation of IKKα that in turn phosphorylates p100 (Senftleben, U. et al, 2001. Science 293:1495-9).

Thus, activation of NF-κB molecules by NIK represents a critical control point for regulation of NF-κB activity.

As described above, disregulated NF-κB activity is associated with the pathogenesis of various major human diseases, such as numerous malignant diseases and diseases associated with pathological immune responses (reviewed in Yamamoto and Gaynor, 2001. J Clin Invest. 107:135-142). For example, activation of the NF-κB pathway is prominently involved in the pathogenesis of chronic inflammatory disease, such as asthma, and rheumatoid arthritis (Tak and Firestein, 2001. J Clin Invest. 107:7-11; Karin, M. and Ben-Neriah, Y., 2000. Annu Rev Immunol. 18:621-63), and inflammatory bowel disease. In addition, altered NF-κB regulation appears to be involved in the pathogenesis of other diseases, such as atherosclerosis (Collins and Cybulsky, 2001. J Clin Invest. 107:255-64; Leonard, W. J. et al., 1995. Immunol Rev. 148: 97-114) and Alzheimer's disease (Mattson and Camandola, 2001. J Clin Invest. 107:247-54; Lin, X. et al., 1999. Immunity 10:271-80), in which the inflammatory response is at least partially involved.

Several lines of evidence indicate that NF-κB activation of cytokine genes is an important contributor to the pathogenesis of asthma, which is characterized by the infiltration of inflammatory cells and the deregulation of many cytokines and chemokines in the lung (Ling, L. et al., 1998. Proc Natl Acad Sci USA. 95:3792-7). Cytokines, such as TNF, that activate NF-κB are elevated in the synovial fluid of patients with rheumatoid arthritis and contribute to the chronic inflammatory changes and synovial hyperplasia seen in the joints of these patients (Malinin, N. L. et al., 1997. Nature 385:540-4). The administration of antibodies directed against TNF or a truncated TNF receptor that binds to TNF can markedly improve the symptoms of patients with rheumatoid arthritis.

Increases in the production of proinflammatory cytokines by both lymphocytes and macrophages have also been implicated in the pathogenesis of inflammatory bowel diseases, including Crohn's disease and ulcerative colitis (Matsumoto, M. et al., 1999. J Immunol. 163:1584-91). NF-κB activation is seen in mucosal biopsy specimens from patients with active Crohn's disease and ulcerative colitis. Treatment of patients suffering from inflammatory bowel diseases with steroids decreases NF-κB activity in biopsy specimens and reduces clinical symptoms. These results indicate that stimulation of the NF-κB pathway is involved in the enhanced inflammatory response associated with these diseases.

Atherosclerosis is triggered by numerous insults to the endothelium and smooth muscle of the damaged vessel wall (Matsushima et al., 2001). A large number of growth factors, cytokines, and chemokines released from endothelial cells, smooth muscle, macrophages, and lymphocytes are involved in this chronic inflammatory and fibroproliferative process (Matsushima, A. et al., 2001. J Exp Med. 193:631-6). NF-κB regulation of genes involved in the inflammatory response and in the control of cellular proliferation is widely understood as playing an important role in the initiation and progression of atherosclerosis.

As described above, abnormalities in the regulation of the NF-κB pathway have been shown to be involved in the pathogenesis of Alzheimer's disease. For example, NF-κB immunoreactivity is found predominantly in and around early neuritic plaque types in Alzheimer's disease, whereas mature plaque types show vastly reduced NF-κB activity (Mercurio F. and Manning A. M., 1999. Curr Opin Cell Biol. 11:226-32). Thus, NF-κB activation is in the initiation of neuritic plaques and neuronal apoptosis during the early phases of Alzheimer's disease. These data therefore indicate that activation of the NF-κB pathway plays a role in a number of diseases that have an inflammatory component involved in their pathogenesis.

In addition to a role in the pathogenesis of diseases associated with disregulated immune responses, hyper-activation or constitutive activation of the NF-κB pathway has also been implicated in the pathogenesis of various human cancers. Abnormally high and/or constitutive activation of the NF-κB pathway is frequently seen in a variety of human malignancies including leukemias, lymphomas, and solid tumors (Miyawaki, S. et al., 1994. Eur J Immunol. 24:429-34). These abnormalities result in abnormally and/or constitutively high levels of NF-κB in the nucleus of a variety of tumors including breast, ovarian, prostate, and colon cancers. The majority of these changes are likely due to alterations in regulatory proteins that activate signaling pathways that lead to activation of the NF-κB pathway. However, mutations that inactivate IκB proteins, in addition to amplification and rearrangements of genes encoding NF-κB family members, can result in the enhanced nuclear levels of NF-κB seen in some tumors (Emmerich et al. Blood November 1; 94 (9):3129-34, 1999).

Since, as described above, NIK is critical for activation of NF-κB, one potentially potent strategy for regulating activation of NF-κB, and thereby for treating diseases associated with disregulated NF-κB activity, involves identifying antibodies capable of specifically binding NIK or a specific portion thereof, and of thereby preventing or inhibiting activation of NF-κB by NIK. By virtue of enabling specific detection of NIK or a specific portion thereof, such antibodies would further enable characterization of aspects of normal/pathological biological/biochemical processes/states involving NIK or a specific portion thereof.

Various prior art approaches attempting to use antibodies for specifically binding NIK have been proposed (see Table 2).

One approach has attempted using mouse monoclonal IgG antibodies for specifically binding amino acid residues 700-947 of the carboxy-terminal region of the NIK polypeptide.

Another approach has attempted employing goat polyclonal antibodies for specifically binding the amino-terminal region of the NIK protein.

Yet another approach has attempted utilizing Rabbit polyclonal antibodies for specifically binding amino acid residues 700-947 or 931-947 of the carboxy-terminal region of the NIK polypeptide.

However, all of the aforementioned approaches suffer from significant disadvantages. Prior art antibodies cannot bind NIK, or a specific portion thereof, with optimal affinity, specificity, and/or versatility. For example, prior art NIK-binding antibodies are incapable of specifically binding any portion of the kinase domain of NIK, or of specifically binding numerous portions of the carboxy- and amino-terminal regions, such as portions thereof involved in NIK activity. Hence, since activation of NF-κB involves NIK-mediated phosphorylation events, prior art antibodies are not suitable for preventing or inhibiting the kinase activity of NIK. Prior art polyclonal antibody preparations are further hampered by their having been raised against suboptimally large NIK segments, and thereby by including antibodies specific for a suboptimally broad range of epitopes (for example, refer to Table 2, below). Furthermore, prior art non-mouse derived/ anti-amino-terminal region antibodies cannot be specifically bound by anti-mouse antibody ligands which constitute the most widely employed type of secondary labeling reagents used in antibody-based detection assays. As such, prior art anti-amino terminal region antibodies are suboptimal for detecting the amino-terminal region of NIK.

Thus, all prior art approaches have failed to provide antibodies capable of binding NIK, or a specific portion thereof, with an affinity, specificity and/or versatility enabling optimal regulation of NIK activity, and hence of NF-κB activity, and/ or enabling optimal detection of NIK.

There is thus a widely recognized need for, and it would be highly advantageous to have, antibodies devoid of the above limitations.

SUMMARY OF THE INVENTION

The invention relates to an antibody or antibody preparation comprising one or more polyclonal, monoclonal, chimeric, humanized, human or anti-anti-idiotype antibodies and/or fragments thereof being capable of specifically binding an amino acid sequence, or a portion of said amino acid sequence such as SEQ ID NO: 1, 2, 3, 4, 5, 6, 7, 8, 9, 10, 11, 12, 13, 15, 18, 19, 20, or 22, and/or 15, preferably SEQ ID NO: 7, 11, 12, 13 and/or 15 and/or an amino acid sequence located in the flanking region of the NIK kinase domain.

In one embodiment, the antibody is of the IgG class and/or antibody fragments such as a single-chain Fv, an Fab, an Fab', an F(ab')2, and a CDR.

In one aspect of the invention, the antibody or antibody preparation is further capable of specifically detecting NIK or a mutein, functional derivative, active fraction, circularly permutated derivative, salt or a portion thereof e.g. by Western immunoblotting analysis, ELISA, immunoprecipitation and/ or capable of regulating a biochemical activity of a NIK molecule.

In a further embodiment, the antibody and/or antibody preparation is capable of regulating a biochemical activity of a NIK molecule.

In a further embodiment, the invention relates to a preparation comprising one or more polyclonal, monoclonal, chimeric, humanized, human or anti-anti-idiotype antibodies and/or fragments thereof being capable of specifically binding NIK or a mutein, functional derivative, active fraction, circularly permutated derivative or salt thereof, the antibody prepared by immunizing a mammal with a peptide comprising an amino acid sequence, or a portion of said amino acid sequence set forth SEQ ID NO: 7, preferably capable of detecting and/or inhibiting other NIK species such as murine NIK.

An embodiment of the invention relates to a monoclonal antibody generated by hybridoma clone Pep 7-81.1 deposited at the CNCM under No. I-3092, or by clone Pep 11-355.8 deposited at the CNCM under No. I-3093 or by clone Pep 12-629-62-18 deposited at the CNCM under No. I-3095, and the respective hybridomas generating the antibodies.

An embodiment of the invention provides, a pharmaceutical composition comprising a pharmaceutically acceptable carrier and, as an active ingredient, an antibody preparation or an antibody according to the invention.

A further embodiment the invention teaches a method for regulating a biochemical activity of a NIK molecule, the method comprising contacting the NIK molecule with a preparation of an antibody or antibody fragment according to the invention.

In a further embodiment, the invention relates to a composition-of-matter comprising a substrate e.g. an affinity chromatography matrix, a carbohydrate (e.g. agarose, sepharose, and cellulose), bead, a resin, or a plastic surface, covalently attached to a polypeptide including an amino acid sequence, or a portion of said amino acid sequence, said amino acid sequence being set forth in SEQ ID NO: 1, 2, 3, 4, 5, 6, 7, 8, 9, 10, 11, 12, 13, 15, 18, 19, 20, or 22 for selectively capturing the antibody or antibody fragment capable of specifically binding the target antigen.

In another further embodiment, the invention relates to a method of treatment of a disease caused or aggravated by the activity of NIK, comprising the administration of an antibody or preparation according to the invention to an individual in need.

In another further embodiment, the invention relates to the use of an antibody or preparation according to the invention, in the manufacture of a medicament for the treatment of a disease caused or aggravated by the activity of NIK.

In another further embodiment, the invention relates to a method for preparing a monoclonal antibody according to the invention comprising growing a cloned hybridoma comprising a spleen cell from a mammal immunized with an amino acid sequence, or a portion of said amino acid sequence, said amino acid sequence is selected from SEQ ID NO: 1, 2, 3, 4, 5, 6, 7, 8, 9, 10, 11, 12, 13, 15, 18, 19, 20, or 22, and a homogeneic or heterogeneic lymphoid cell in liquid medium or mammalian abdomen to allow the hybridoma to produce and accumulate the monoclonal antibody.

In another embodiment, the invention relates to a method for preparing a monoclonal antibody comprising immunizing a mammal with a peptide, which is part of an amino acid sequence of NIK, and is selected from SEQ ID NO: 1, 2, 3, 4, 5, 6, 7, 8, 9, 10, 11, 12, 13, 15, 18, 19, 20, or 22.

In another embodiment, the invention relates to a method for the purification of a NIK binding protein, which comprises contacting a sample containing NIK and the NIK-binding protein with antibody or antibody preparation, co-immunoprecipitating the NIK and NIK-binding protein, washing the immune complex produced, and recovering the NIK-binding protein from the immune complex using a competing peptide derived from NIK.

In another embodiment, the invention teaches the use of an antibody preparation or an antibody according to the invention, for the immune purification of NIK or a mutein, functional derivative, active fraction, circularly permutated derivative or salt thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2 shows a sequence diagram depicting the amino acid sequence of human NIK (SEQ ID NO: 21). The NIK-derived peptides used for immunizations are underlined (Note: peptides shown not having a Cys residue at the N-terminus were synthesized with a supplementary Cys residue at the N-terminus and were used for immunizations as such).

FIGS. 4a-d shows photographs of a Western immunoblotting analysis depicting the capacity of sera from mice immunized with the indicated NIK-derived peptides to detect NIK with very high sensitivity in protein-G-immunoprecipitated protein lysate from PCS3MTNIK-transfected cells. The assays shown in FIGS. 4a-d were performed in parallel, and anti-myc-tag antibody was used as a positive control (FIG. 4d).

DESCRIPTION OF THE PREFERRED EMBODIMENTS

Figure 1:
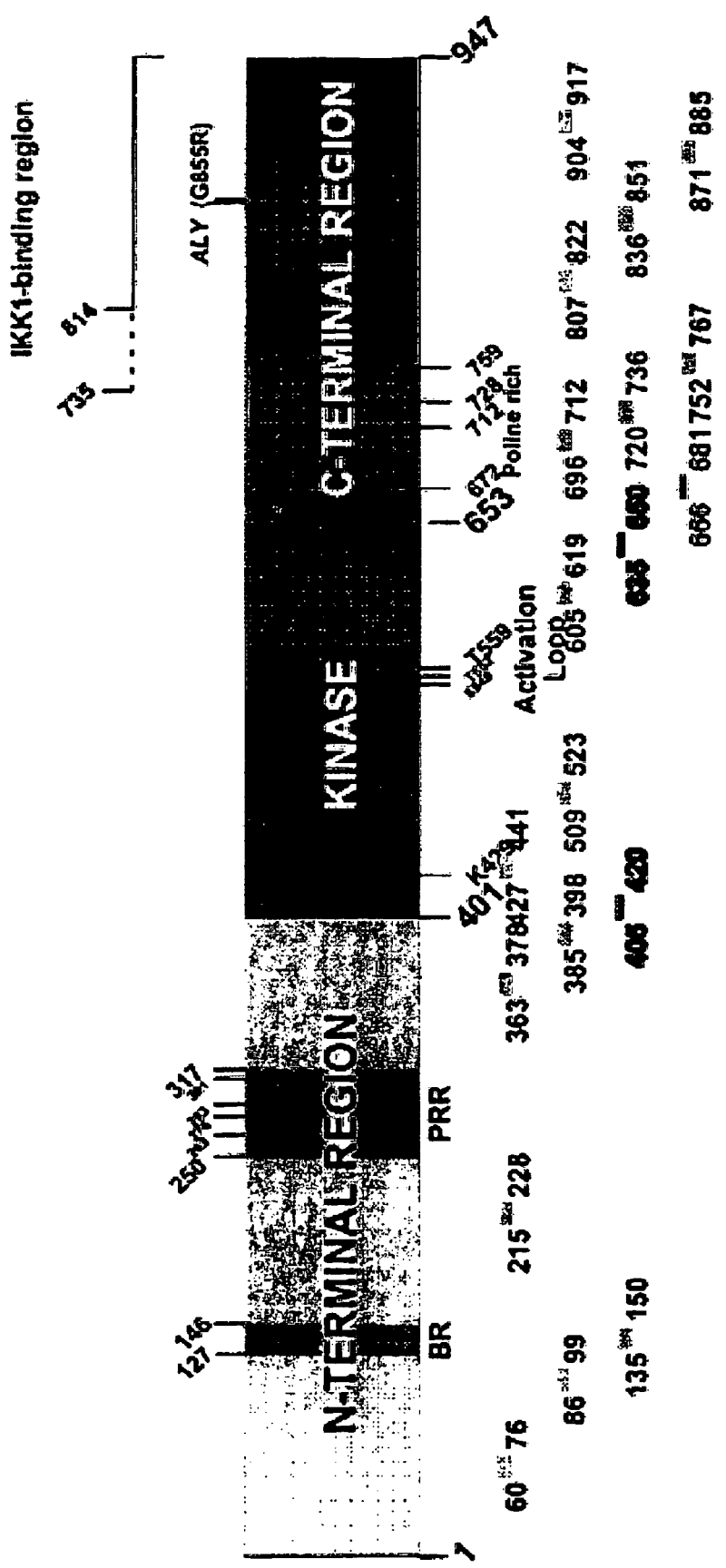
FIG. 1 shows a schematic diagram depicting the NIK polypeptide, regions thereof, and the positioning therein of the NIK-derived peptides used for immunizations.

The present invention relates to an antibody or anitbody fragment preparation capable of specifically binding NF-KBinducing kinase (NIK)/MAP3KI4, or a specific portion thereof. Specifically, the present invention can be used for regulating a biochemical activity, such as a kinase activity, of NIK, and for specifically detecting NIK or a specific portion thereof. By virtue of enabling such regulation and such detection, the preparation can be used, respectively, for regulating NF-κB activation, and hence for treating a disease associated with deregulated NF-κB activity, and for characterizing aspects of normal/pathological biological/biochemical processes/states involving NIK or a specific portion thereof.

Before explaining at least one embodiment of the invention in detail, it is to be understood that the indention is not limited in its application to the details set forth in the following descripiion or exemplified by the Examples. The invention is capable of other embodiments or of being practiced or carried out in various ways. Also, it is to be understood that the phraseology and terminologv employed herein is for the purpose of description and should not be regarded as limiting.

No treatment, or no satisfactory treatment, is available for numerous lethal and/or highly debilitating diseases associated with disregulated NF-κB activity. Such diseases include malignant diseases and diseases, such as autoimmune, allergic, inflammatory, transplantation-related diseases, which are associated with pathological immune responses. Since NIK is a critical activator of NF-κB, one potentially potent strategy for treating a disease associated with disregulated NF-κB activity involves identifying antibodies capable of specifically binding NIK or a specific portion thereof, and using such antibodies for therapeutically regulating NF-κB activity. By virtue of enabling specific detection of NIK or 'a specific portion thereof, such antibodies would also enable characterization of aspects of normal/pathological biological/biochemical processes/states involving NIK or a specific portion thereof.

While reducing the present invention to practice, an antibody preparation was unexpectedly generated capable of: (i) specifically binding NIK, or a specific portion thereof, such as the kinase region or a specific portion thereof, or a specific portion of the amino- or carboxy-terminal region; or (ii) optimally specifically binding NIK, or a specific portion thereof, such as the kinase region or a specific portion thereof, or a specific portion of the amino- or carboxy-terminal region. The capacity of the antibody preparation of the present invention to specifically bind the whole kinase region or any specific portion thereof, or to specifically bind any of various specific portions of the amino- or carboxy-terminal regions of NIK is unique relative to all prior art antibodies.

Hence, in sharp contrast to prior art antibodies, the antibody preparation of the present invention can be used for optimally regulating a biochemical activity, such as a kinase activity of NIK or a specific portion thereof, and for optimally detecting NIK or a specific portion thereof. The antibody of the invention can also be used to co-immunoprecipitate and isolate regulatory factors binding NIK.

It will be appreciated by the ordinarily skilled artisan that an antibody preparation such as the one of the present invention can be treated using standard methods, for example as described hereinbelow, so as to generate a preparation of one or more types of antibody fragment having antigen-binding characteristics essentially identical as those of the untreated antibody preparation.

Thus, according to one aspect of the present invention, there is provided a preparation of an antibody or antibody fragment capable of specifically binding an amino acid sequence, or a portion thereof, where the amino acid sequence is set forth in SEQ ID NO: 1, 2, 3, 4, 5, 6, 7, 8, 9, 10, 11, 12, 13, 15, 18, 19, 20, and/or 22.

Preferably, binding the portion of the peptide of amino acid sequence set forth in SEQ ID NO: 7, 8, 11, 12, 13 and 15 or to a portion thereof. More preferably, binding the portion of the peptide of amino acid sequence set forth in SEQ ID NO: 7, 11 and 12.

The term "a portion of a peptide" is defined as at least a tripeptide of SEQ ID NO:22.

The amino acid sequence set forth in SEQ ID NO: 1, 2, 3, 4, 5, 6, 7, 8, 9, 10, 11, 12, 13, 15, 18, 19, 20, or 22, or a portion of such an amino acid sequence is referred to hereinafter as "target antigen".

As described hereinbelow, the preparation can be used for optimally regulating a biochemical activity of NF-κB inducing kinase (NIK)/MAP3K14, such as a kinase activity, and hence can be used for optimally regulating activation of NF-κB, and thereby can be used for optimally treating a disease associated with deregulation of NF-κB activity. Furthermore, the preparation can be uniquely used for detecting the kinase region of NIK, or any of various specific portions thereof, and can be used for optimally detecting any of various specific portions of the amino- or carboxy-terminal region of NIK. As such the preparation can be utilized for optimally characterizing aspects of normal/pathological biological/biochemical processes/states involving NIK or specific portions thereof.

As used herein, the term "treating" when relating to a disease refers to preventing onset of a disease, alleviating a disease, attenuating or eliminating the symptoms of a disease, slowing or reversing the progression of a disease, or curing a disease.

Depending on the application and purpose, the preparation of the present invention may advantageously comprise any of various combinations of antibody or antibody fragment populations, and may advantageously comprise an antibody or antibody fragment characterized by any of various combinations of structural and/or functional characteristics. For example, the preparation may advantageously comprise: (i) a population of antibodies and/or antibody fragments capable of specifically binding any of various combinations of target antigens of the present invention; (ii) an antibody or antibody fragment capable of specifically binding any of various specific portions of the amino acid sequence set forth in SEQ ID NOs: 1, 2, 3, 4, 5, 6, 7, 8, 9, 10, 11, 12, 13, 15, 18, 19, or 20; and/or (iii) an antibody or antibody fragment attached to any of various detectable molecules.

As used herein, the term "antibody" refers to a substantially whole or intact antibody molecule.

As used herein, the phrase "antibody fragment" refers to a molecule comprising a portion of an antibody capable of specifically binding an antigen, an antigenic determinant or an epitope.

As described in the Examples section, below:

(i) the amino acid sequence set forth in SEQ ID NO: 1, 2, 3, 4, 5, or 6 represents amino acid residues 60-76, 86-99, 135-150, 215-228, 363-378, or 385-398 of human NIK, respectively, and is located in the amino-terminal region of human NIK;

(ii) the amino acid sequence set forth in SEQ ID NO: 22 represents amino acid residues 401-681 of human NIK correspond to the kinase region of human NIK and nearby the kinase region, and;

(iii) SEQ ID NO: 7, 8, 9, 10, 11 or 12 represents amino acid residues 405-420, 427-441, 509-523, 605-619, 635-650 or 666-681 of human NIK, respectively, and is located in the kinase region or nearby the kinase region of the human NIK; and (iv) SEQ ID NO: 12, 13, 15, 17, 18, 19, or 20 represents amino acid residues 696-712, 752-767, 836-851, 871-885, or 904-917 of human NIK, respectively, and is located in the carboxy-terminal region of human NIK.

Preferably, the preparation is capable of binding the target antigen with maximal affinity.

While reducing the present invention to practice, different antibody preparations were unexpectedly generated with the following properties:

Antibody having binding capacity to "flanking region of NIK kinase domain" e.g. to peptides of the N terminal region of the kinase domain and preferably to peptides 405-420 (SEQ ID NO:7 and antibodies having binding capacity to peptides at or near the C-terminal region of the kinase domain, and preferably to peptides 635-650 (SEQ ID NO:11) and 666-681 (SEQ ID NO:12) or having binding capacity to a portion of such peptides, are capable of efficiently detect NIK by Western immunoblotting analysis is.

Antibody having binding capacity to peptides in the ATP binding region of NIK and preferably to peptide 427-441 (SEQ ID NO: 8), or having binding capacity to a portion of such peptides are capable of efficiently detect NIK by ELISA.

Antibody having binding capacity to the peptides near and at the beginning of the C terminal region e.g. within residues 635-767 and preferably to peptides 635-650 (SEQ ID NO:11 and 66-681 (SEQ ID NO: 12), 696-712 (SEQ ID NO:13) and 752-767 (SEQ ID NO:15), or having binding capacity to a portion of such peptides are capable of efficiently immunoprecipitate NIK.

Antibody having binding capacity to peptides at or near the C-terminal region of the kinase domain, and preferably to peptides 635-650 (SEQ ID NO:11) and 666-681 (SEQ ID NO:12) or having binding capacity to a portion of such peptides, are capable of efficiently detect NIK by both Western immunoblotting analysis and immunoprecipitation.

In general, a preparation of the present invention capable of binding the target antigen with maximal affinity will enable optimal down-regulation of a biochemical activity mediated or associated with the target antigen. Similarly, a preparation of the present capable of specifically binding the target antigen with maximal affinity will generally enable detection of the target antigen with optimal sensitivity.

By virtue of the above-described capacity of the preparation for specifically binding a target antigen of the present invention, in particular by virtue of the unique capacity of the preparation for specifically binding a target antigen of the present invention located in a functional region of NIK, the preparation can be used for down-regulating a biochemical activity of NIK. In particular, by virtue of the above-described unique capacity of the preparation for specifically binding a target antigen of the present invention located in the kinase region of NIK, the preparation can be used for optimally down-regulating kinase activity of NIK. It will be appreciated that since such kinase activity is crucial for activating nuclear factor (NF)-κB, as described above, a preparation of the present invention capable of optimally down-regulating such kinase activity can be used for optimally down-regulating activity of NF-κB.

The NF-κB proteins is a family of proteins that share a 300 amino acid domain, the "Rel homology domain". The Rel homology domain mediates the DNA binding, dimerization, and nuclear transport of NF-κB proteins. In addition to the Rel homology domain, some members of the the NF-κB family also contain a transactivation domain (e.g. c-Rel, RelB, and and p65). The NF-κB members p50 and p52, are produced upon activation by lysis of inactive precursors p105 and p100, respectively. P50 and p52c have DNA binding dimerization properties but not strong transactivation domains. It is the differential generation of these proteins, their ability to heterodimerize with different family members, and the interaction of these proteins with different components of the transcription apparatus that contribute to the diverse effects of activating the NF-κB pathway. NIK does not affect all NF-κB species but only specific NF-κB species e.g. it induces degradation of p100 and generation of p52c, in response to specific inducers e.g. lymphotoxin. Modulation of NIK, e.g. using the antibodies of the invention, is therefore likely to affect specific aspects of the pathological implications NF-κB activation. This is an advantage since general non-specific inhibition of NF-κB is dangerous, for example, it can result in extensive apoptosis in the liver.

As used herein the phrase "down-regulating" when relating to a biochemical activity refers to preventing, reducing, or inhibiting such a biochemical activity.

When employed for inhibiting a biochemical activity of NIK, the preparation is preferably capable of specifically binding a maximal number of target antigens within a portion of NIK associated with such biochemical activity. In particular, when employed for inhibiting kinase activity of NIK, the preparation is preferably capable of specifically binding a maximal number of target antigens located within the NIK kinase region amino acid sequences set forth in SEQ ID NOs: 7, 8, 9, 10, 11, 12, 13 and 15, more preferably capable of specifically binding a maximal number of target antigens located within the NIK kinase region amino acid sequences set forth in SEQ ID NOs: 7, 11 and 12. While a preparation of the present invention capable of specifically binding only one target antigen located within a functional region of NIK, such as the kinase region, may be employed for efficiently inhibiting a biochemical function of NIK, such as kinase activity, associated with such a functional region, a preparation capable of specifically binding a maximal number of target antigens located within such a functional region will more effectively down-regulate the kinase activity by virtue of interfering with a maximal number of functional epitopes within the functional region.

Alternately, for inhibiting kinase activity of NIK, the preparation may be advantageously capable of specifically binding a maximal number of target antigens located within the amino acid sequences set forth in SEQ ID NO: 1, 2, 3, 4, 5, 6, 7, 8, 9, 10, 11, 12, 13, 15, 18, 19, and 20.

By virtue of the above-described capacity of the preparation for specifically binding a target antigen of the present invention, the preparation can be used for specifically detecting NIK with optimal sensitivity relative to prior art methods, and can uniquely be used for specifically detecting NIK and or a target antigen of the present invention such as the amino acid sequence set forth in SEQ ID NO: 1, 2, 3, 4, 5, 6, 7, 8, 9, 10, 11, 12, 13, 15, 18, 19, or 20.

The preparation can be used for essentially any application benefiting from a reagent capable of binding a target antigen of the present invention with optimal affinity. Such applications include, for example, affinity purification, and hence identification and characterization, of specific ligands of NIK.

As is described and illustrated in the Examples section which follows, a preparation of the present invention capable of specifically binding the amino acid sequence set forth in SEQ ID NO: 1, 2, 3, 4, 5, 6, 7, 8, 9, 10, 11, 12, 13, 15, 18, 19, or 20 can be used for specifically detecting, according the guidance set forth therein, the amino acid sequence set forth in SEQ ID NO: 1, 2, 3, 4, 5, 6, 7, 8, 9, 10, 11, 12, 13, 15, 18, 19, or 20, respectively.

Preferably, a preparation of the present invention capable of specifically binding a target antigen of the present invention is derived from sera of animals immunized with such a target antigen (referred to hereinafter as "anti-sera"). As is described and illustrated in the Examples section below, an anti-serum of the present invention capable of specifically binding the amino acid sequence set forth in SEQ ID NO: 1, 2, 3, 4, 5, 6, 7, 8, 9, 10, 11, 12, 13, 15, 18, 19, or 20 can be generated by immunizing a mammal with the target antigen according to the protocol set forth therein. Further guidance for generating the preparation by immunization of a mammal is provided hereinbelow.

Guidance for obtaining a polypeptide such as the target antigen is provided hereinbelow.

A preparation of the present invention capable of specifically binding a set of different target antigens of the present invention may be obtained by pooling a set of preparations of the present invention collectively capable of specifically binding each target antigen of the set of target antigens, where each preparation of the pool is derived from sera of animals immunized with a single target antigen of the set of target antigens. Alternatively, the preparation capable of specifically binding the set of target antigens may be obtained by pooling a set of preparations of the present invention collectively capable of specifically binding each target antigen of the set of target antigens, where at least one of the pooled preparations is derived from sera of animals immunized with at least two target antigens of the set of target antigens. For example, a preparation of the present invention capable of specifically binding a set of target antigens of the present invention may be derived from the serum of animals conveniently simultaneously immunized with all of the target antigens of the set of target antigens.

Depending on the application and purpose, the preparation may be advantageously employed in the form an unpurified anti-serum, or it may be purified in various ways prior to use. For example, the preparation may be used in the form of a purified: (i) preparation of an antibody of a specific isotype, or set of isotypes; (ii) preparation of an antibody or antibody fragment capable of specifically binding a specific portion of the amino acid sequence set forth in SEQ ID NO: 1, 2, 3, 4, 5, 6, 7, 8, 9, 10, 11, 12, 13, 15, 18, 19, or 20; and/or (ii) preparation of an antibody or antibody fragment capable of binding with a desired affinity a target antigen of the present invention.

A preparation of the present invention in the form of an unpurified anti-serum can be convenient and satisfactory for use in various applications. For example, as is described and illustrated in the Examples section below, an unpurified anti-serum of the present invention, in particular an unpurified anti-serum generated by immunization with the amino acid sequence set forth in SEQ ID NO: 7 or 11 can be used for efficiently detecting NIK via Western immunoblotting analysis, and an unpurified anti-serum generated by immunization with the amino acid sequence set forth in SEQ ID NO: 8 can be used for efficiently detecting NIK via ELISA. In general, for applications benefiting from a preparation of the present invention capable of binding a target antigen of the present invention with a range of affinities/specificities is desirable, an unpurified preparation of the present invention, such as an anti-serum of the present invention, will be advantageous. Such an unpurified preparation may often be adequate for a given application since the heterogeneity of the polyclonal antibody or antibody fragment mixture contained therein will often include one or more antibodies or antibody fragments having an adequate binding affinity/specificity for the target antigen.

Alternately, a purified antibody or antibody fragment of the present invention may be advantageously employed in applications such as those involving administration of the antibody or antibody fragment to an individual, and in those in which detection of the target antigen with optimal sensitivity is desirable.

As used herein, the term "individual", refers to a human.

For example, an IgG antibody preparation of the present invention may be advantageously purified from an anti-serum of the present invention using protein-G affinity purification, preferably via protein-G immunoprecipitation. As is described and illustrated in the Examples section which follows, an anti-serum of the present invention derived from an animal immunized with the amino acid sequence set forth in SEQ ID NO: 1, 2, 3, 4, 5, 6, 7, 8, 9, 10, 11, 12, 13, 15, 18, 19, or 20 and purified via protein-G immunoprecipitation according to the protocol set forth therein, can be used for detecting with optimal sensitivity, via Western immunoblotting analysis, the amino acid sequence set forth in SEQ ID NO: 1, 2, 3, 4, 5, 6, 7, 8, 9, 10, 11, 12, 13, 15, 18, 19, or 20, respectively.

A purified antibody or antibody fragment of the present invention capable of specifically binding the target antigen can be advantageously used for regulating with optimal specificity a biochemical activity of NIK associated with the target antigen, and for detecting the target antigen with optimal specificity. In particular, a purified antibody or antibody fragment of the present invention capable of specifically binding a target antigen of the present invention comprised within the amino acid sequence set forth in SEQ ID NO: 7, 8, 9, 10, 11, 12, 13, and 15 can be advantageously used for regulating kinase activity of NIK with optimal specificity. In general, for applications benefiting from optimal reproducibility, standardization, or precision, a purified antibody or antibody fragment of the present invention capable of specifically binding the target antigen will generally be optimal relative to an unpurified preparation of the present invention.

Purifying the antibody or antibody fragment capable of specifically binding the target antigen can be achieved, for example, by purifying a preparation of the present invention, such as an unpurified anti-serum of the present invention, via affinity chromatography using a substrate covalently attached to the target antigen. Such a substrate-attached target antigen can be used, according to standard affinity chromatography methodology, for selectively capturing the antibody or antibody fragment capable of specifically binding the target antigen.

The substrate is preferably an affinity chromatography matrix. An affinity chromatography matrix, being a substrate optimized for performing affinity chromatography, may be advantageously employed for achieving optimal affinity purification.

Substrates having various structural and chemical characteristics may be employed for performing the purification.

Preferably, the substrate comprises a carbohydrate or a derivative thereof. Preferably, the carbohydrate is agarose, sepharose, or cellulose.

Preferably, the substrate is a bead, a resin, or a plastic surface.

Substrates such as beads, resins, or plastic surfaces comprising carbohydrates such as agarose, sepharose or cellulose are routinely used for practicing affinity chromatography in the art.

Ample guidance for practicing affinity chromatography, such as that employing such substrates, is provided in the literature of the art (for example, refer to: Wilchek M. and Chaiken I., 2000. Methods Mol Biol. 147:1-6; Jack G W. Immunoaffinity chromatography. Mol Biotechnol 1, 59-86; Narayanan S R., 1994. Journal of Chromatography A 658: 237-258; Nisnevitch M. and Firer M A., 2001. J Biochem Biophys Methods 49:467-80; Janson J C. & Kristiansen T. in:

"Packings and Stationary Phases in Chromatography Techniques" (ed. Unger, K K.) pp. 747 (Marcel Dekker, New York, 1990); Clonis, Y. D. in: "HPLC of Macromolecules: A Practical Approach", pp. 157 (IRL Press, Oxford, 1989); Nilsson J. et al., 1997. Protein Expr Purif. 11:1-16).

Alternately, a preparation of the present invention can be purified using a variety of standard protein purification techniques, such as, but not limited to, ion exchange chromatography, filtration, electrophoresis, hydrophobic interaction chromatography, gel filtration chromatography, reverse phase chromatography, concanavalin A chromatography, chromatofocusing and differential solubilization.

An antibody or antibody fragment of the present invention capable of specifically binding a target antigen of the present invention with a desired affinity can be advantageously used for achieving a desired level of regulation of a biochemical activity of NIK associated with the target antigen, and can advantageously be used for detecting the target antigen with desired sensitivity. In particular, an antibody or antibody fragment of the present invention capable of specifically binding with maximal affinity a target antigen of the present invention comprised in the kinase region of NIK can be advantageously used for optimally down-regulating kinase activity of NIK. Similarly, an antibody or antibody fragment of the present invention capable of specifically binding the target antigen with maximal affinity can be advantageously used for detecting the target antigen with optimal sensitivity.

Purifying the antibody or antibody fragment capable of binding the target antigen with a desired affinity from a preparation of the present invention, such as an unpurified antiserum of the present invention, can be achieved, for example, via affinity chromatography purification of an unpurified—or more preferably a protein-G purified-anti-serum of the present invention, by using the target antigen as an affinity ligand, and via selective elution of a substrate-bound antibody or antibody fragment under conditions of controlled stringency (for example under conditions of controlled pH and/or salt concentration). In particular, an antibody or antibody fragment of the present invention capable of binding the target antigen with a maximal affinity may be conveniently obtained by elution under conditions of effectively maximal stringency (for example under conditions of effectively maximal or minimal pH and/or maximal salt concentration). Typically, an antibody or antibody fragment may be bound to a substrate-attached cognate antigen thereof under conditions of physiological pH and salt concentration, and such an antibody or antibody fragment may typically be eluted from the substrate by decreasing the pH to 2.5 or lower, or by increasing the pH to 11 or higher.

It will be appreciated by the ordinarily skilled artisan that an antibody or antibody fragment having an affinity characterized by a dissociation constant of up to $10^{-12}$ for a cognate antigen can be obtained using common art techniques.

As described hereinabove, the preparation may advantageously comprise an antibody or antibody fragment attached to any of various types of detectable molecule.

A preparation of the present invention comprising an antibody or antibody fragment attached to a detectable molecule can be used for detecting the target antigen specifically bound by the antibody or antibody fragment.

The preparation may comprise an antibody or antibody fragment attached to any of numerous types of detectable molecule, depending on the application and purpose.

For example, depending on the application and purpose, the detectable molecule may advantageously be a fluorophore, an enzyme, a light-emitting molecule, or a radioisotope.

Preferably, the detectable molecule is an enzyme.

An enzyme may be advantageously utilized for enabling detection of the target antigen via any of various enzyme-based detection methods. Examples of such methods include, but are not limited to, enzyme linked immunosorbent assay (ELISA; for example, for detecting the target antigen in a solution), enzyme-linked chemiluminescence assay (for example, for detecting the complex in an electrophoretically separated protein mixture), and enzyme-linked histochemical assay (for example, for detecting the complex in a fixed tissue).

As is described and illustrated in the Examples section below, a preparation of the present invention comprising an antibody attached to an enzyme can be used for efficiently detecting NIK via Western immunoblotting analysis or ELISA.

Numerous types of enzymes may be employed for detecting the target antigen, depending on the application and purpose.

Examples of suitable enzymes include, but are not limited to, horseradish peroxidase (HPR), β-galactosidase, and alkaline phosphatase (AP).

Ample guidance for practicing enzyme-based molecular detection methods is provided in the literature of the art (for example, refer to: Khatkhatay MI. and Desai M., 1999. J Immunoassay 20:151-83; Wisdom GB., 1994, Methods Mol Biol. 32:433-40; Ishikawa E, et al., 1983. I Immunoassay 4:209-327; Oellerich M., 1980, J Clin Chem Clin Biochem. 182197-208; Schuurs AH, and van Weemen BK., 1980, J Immunoassay 1:229-49).

A preparation of the present invention comprising an antibody or antibody fragment attached to a fluorophore may be advantageously employed for detecting the target antigen via any of numerous fluorescence-based molecular detection methods. Depending on the application and purpose, such methods include, but are not limited to, fluorescence activated flow cytometry (FACS; for example for characterizing expression or display of the target antigen in a suspended cell population), fluorescence confocal microscopy (for example, for detecting the molecule in a dead or living cell or tissue in three dimensions), fluorescence in-situ hybridization (FISH), fluorescence resonance energy transfer (FRET; for example, for detecting a specific intermolecular association involving the target antigen), fluorescence histochemistry (for example, for detecting the molecule in a fixed histological sample), and the like.

Various types of fluorophores, depending on the application and purpose, may be employed for detecting the target antigen.

Examples of suitable fluorophores include, but are not limited to, phycoerythrin, fluorescein isothiocyanate (FITC), Cy-chrome, rhodamine, green fluorescent protein (GFP), blue fluorescent protein (BFP), Texas red, and the like.

Ample guidance regarding fluorophore selection, methods of linking fluorophores to various types of molecules, such as an antibody or antibody fragment of the present invention, and methods of using such fluorescent immunoconjugates for detecting molecules is available in the literature of the art [for example, refer to: Richard P. Haugland, "Molecular Probes; Handbook of Fluorescent Probes and Research Chemicals 1992-1994", 5th ed., Molecular Probes, Inc. (1994); U.S. Pat. No. 6,037,137 to Oncoimmunin Inc.; Hemianson, "Bioconjugate Techniques", Academic Press New York. N.Y. (1995): Kay M. et al., 1995, Biochemistry 341293; Stubbs et al., 1996, Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350.466 to Targesome, Inc.].

Examples of suitable light-emitting molecules include luminol.

Examples of suitable radioisotopes include [125]iodine, [35]sulfur, [3]hydrogen, [32]phosphorus, etc.

The detectable molecule may be attached to the antibody or antibody fragment in various ways, depending on the application and purpose, and on the nature of the molecules involved. Ample guidance for attaching a detectable molecule to an antibody or antibody fragment is provided in the literature of the art [for example, refer to: "Using Antibodies: A Laboratory Manual", Ed Harlow, David Lane (eds.), Cold Spring Harbor Laboratory Press (1999); also, refer to the extensive guidelines provided by The American Chemical Society, for example at: http://www.chemistry.org/portal/Chemistry]. One of ordinary skill in the art, such as a chemist, will possess the required expertise for suitably practicing such chemical synthesis techniques.

Accordingly, a preparation of the present invention comprising an antibody or antibody fragment attached to a detectable molecule can be used for efficiently and uniquely detecting the target antigen in essentially any context.

The antibody preparation of the invention can be used for immuno purification of NIK or portion thereof, preferably, antibodies of the invention capable of efficiently immunoprecipitating NIK.

In one preferred embodiment, an antibody of the invention can be used for capture step in the purification of NIK or portion thereof.

Depending on the application and purpose, the preparation may advantageously be a preparation of any of various types of antibody fragments.

The antibody fragment is preferably a single-chain Fv (scFv), or more preferably an Fab, Fab', F(ab')$_2$ or CDR.

An antibody fragment has the advantage of being smaller than a parental antibody from which it is derived while retaining substantially identical target-antigen binding specificity, or both binding specificity and binding affinity, as the parental antibody. Thus, an antibody fragment, by virtue of being smaller than the parental antibody, will thereby generally have superior biodistribution, and diffusion properties (for example, systemically in-vivo, or in isolated tissues) than the latter. An antibody fragment substantially lacking an Fc region, such as a single-chain Fv, an Fab', an Fab an F(ab')$_2$ or CDR, is advantageous for applications involving exposure of the preparation to a molecule capable of specifically binding such an Fc region, and in which such binding is undesirable. Typically this may involve an undesired binding of an Fc region exposed to a cognate Fc receptor, or an Fc-binding complement component (for example, complement component C1q, present in serum). Fc receptors are displayed on the surface of numerous immune cell types, including: professional APCs, such as dendritic cells; B lymphocytes; and granulocytes such as neutrophils, basophils, eosinophils, monocytes, macrophages, and mast cells. Thus, the absence of an Fc region from the antibody fragment may be particularly advantageous for avoiding undesired an Fc receptor-mediated immune cell activation or a complement component-mediated complement cascade, particularly when administering the preparation in-vivo to an individual.

An F(ab')$_2$ is a fragment of an antibody molecule containing a divalent antigen-binding portion of an antibody molecule.

An F(ab')$_2$ preparation of the present invention may be conveniently obtained using standard art methods by treating an antibody preparation of the present invention, such as an anti-serum of the present invention, with the enzyme pepsin. The resultant F(ab')$_2$ product is a 5S particle.

An Fab, or Fab' is a fragment of an antibody molecule containing a monovalent antigen-binding portion of an antibody.

CDR is the complementarity determining region of an antibody and the antibody region in contact with the antigen.

An Fab' preparation of the present invention may be conveniently obtained using standard art methods by treating an antibody preparation of the present invention, such as an anti-serum of the present invention, with the enzyme pepsin, followed by reduction of the resultant F(ab')$_2$ into. Such reduction may be effected using a thiol reducing agent, and optionally using a blocking group for the sulfhydryl groups resulting from cleavage of disulfide linkages. Such treatment generates two monovalent 3.5S Fab's an Fc fragment.

An Fab preparation may be conveniently obtained using standard art methods by treating an antibody preparation of the present invention, such as an anti-serum of the present invention, with the enzyme papain to yield the intact light chain and a portion of heavy chain composed of the variable and $C_H1$ domains.

The CDR can be generated e.g. as described in EP0585939 or as described by Strandberg et al. (Protein Eng. 2001 January; 14(1): 67-74). The CDR according to the invention can be a modified CDR, which has enhanced effect on the modulation of NIK. An example for methods of modification of active peptides is described by Sawa et al. 1999 (J. Med. Chem. 42, 3289-3299).

Ample guidance for generating an antibody fragment by enzymatic treatment of an antibody is provided in the literature of the art (for example, refer to: Goldenberg, U.S. Pat. Nos. 4,036,945 and 4,331,647; Porter R R., 1959. Biochem J. 73:119-126).

A single chain Fv (also referred to in the art as "scFv") is a single chain molecule including the variable region of the light chain and the variable region of the heavy chain, linked by a suitable polypeptide linker.

An F(ab')$_2$, Fab', Fab, or single-chain Fv preparation of the present invention may be obtained using recombinant techniques.

Preferably, obtaining a recombinant antibody fragment is effected by isolating mRNA of B lymphocytes of animals immunized with the target antigen, generating CDNA from the mRNA via RT-PCR, and using the cDNA to construct an antibody fragment phage-display library. B lymphocytes can be conveniently isolated from the spleen, or, alternately from the blood, bone-marrow, or lymph nodes of the immunized animal.

Recombinant phages displaying an antibody fragment possessing a desirable target-antigen-binding property can be selected from the library by sequential enrichment of phages having such a binding property from a large excess of non-binding clones. This selection can be achieved using any of various techniques including panning on immobilized target antigen; panning using specific elution; using biotinylated antigen; affinity purification on columns; or direct panning on cells. Following selection, the phages displaying non-specific antibody fragments may be removed by washing and the bound phages, bearing scFv displaying the desired target-antigen binding property, are eluted and amplified by infection of E. coli. Once a recombinant phage displaying an antibody fragment having a desired target antigen-binding property has been isolated, the polynucleotide sequence encoding the variable regions of the antibody fragment can be recovered from the phage display package and cloned into a recombinant prokaryotic or eukaryotic expression vector using standard methodology [for example, refer to: "Current Protocols in Molecular Cloning", Ausubel et al. (eds.), Greene Publishing and Wiley Interscience, New York, N.Y. (1989); Sambrook et al., infra and associated references]. Such a prokaryotic expression vector can be used for producing the purified recombinant antibody fragment in E. coli (for example, refer to Studier et al., 1990. Methods in Enzymol. 185:60-89). Such a eukaryotic expression vector can be used for genetically transforming a eukaryotic cell for expression of the recombinant antibody fragment.

Ample guidance for obtaining and exploiting an antibody fragment-phage display library from B lymphocyte mRNA is provided in the literature of the art [for example, refer to: Hoogenboom et al., 1998. Immunotechnology 4:1-20; Kand et al., 1991. Proc Natl Acad Sci USA. 88:4363; Barbas et al. 1991. Proc Natl Acad Sci USA. 88:7978; Garrard et al., 1991. Biotechnology 9:1373-1377; Hoogenboom et al., 1991. Nucleic Acids Res. 19:4133-4137; Sharon et al., 2000. Combinational Chemistry and High Throughput Screening 3:185-196; U.S. Pat. Nos. 5,698,426, 5,658,727, 5,223,409, 5,403, 484, 5,580,717, 5,427,908, 5,750,753, 5,821,047, 5,571,698, 5,427,908, 5,516,637, 5,780,225, 5,658,727, 5,733,743 and 5,969,108; PCT application No. PCT/GB91/01134; PCT publications WO 90/02809, WO 91/10737, WO 92/01047, WO 92/18619, WO 93/11236, WO 95/15982, and WO 95/20401; Brinkman et al., 1995. J. Immunol. Methods 182: 41-50; Ames et al., 1995. J. Immunol. Methods 184:177-186; Kettleborough et al., 1994. Eur. J. Immunol. 24:952-958; Persic et al., 1997. Gene 187 9-18; and Burton et al., 1994. Advances in Immunology 57:191-280; Pluckthun in: "The Pharmacology of Monoclonal Antibodies", Vol. 113, Rosenburg and Moors (eds.), Springer-Verlag, New York, pp. 269-315 (1994); Hoogenboom et al., 1998. Immunotechnology 4:1-20].

It will be appreciated that the above-described methodology can be used to obtain a monoclonal antibody fragment preparation of the present invention having essentially any desired target antigen-binding affinity and/or specificity. Such a preparation can be utilized in various applications benefiting from a reagent capable of binding the target antigen with such defined target antigen-binding characteristics.

Since an Fab' is essentially similar in structure to an Fab, a preparation of the present invention comprising an Fab' may be employed essentially interchangeably with one comprising an Fab, where such Fab' and Fab comprise essentially the same heavy and light chain variable regions. For applications, as will usually be the case, benefiting from a preparation of the present invention comprising an antibody fragment capable of binding the target antigen with maximal affinity, an F(ab')$_2$ preparation of the present invention may superior to an Fab, Fab' or scFv preparation of the present invention, due to the divalent binding of an F(ab')$_2$ to the target antigen relative to the monovalent binding of such a monovalent antibody fragment.

As mentioned hereinabove, depending on the application and purpose, the antibody or antibody fragment preparation may originate from any of various mammalian species An antibody or antibody fragment preparation of the present invention originating from a desired species may be derived from serum of the animal of such species immunized with the target antigen.

Such an antibody may be monovalent, bivalent or multivalent, it may have cross-linking activity or not. Antibodies used in accordance with the present invention can be polyclonal, such as antibodies produced in the rabbit, or monoclonal antibodies.

Preferably, the invention relates to the use of an antibody preparation selected from the group consisting of polyclonal, monoclonal, chimeric, humanized, human or anti-anti-idiotype antibodies or fragments thereof. Preferably, the antibody or antibody fragment is of mouse origin.

The term "monoclonal antibody" (mAb) is meant to include monoclonal antibodies, chimeric, humanized antibodies, human antibodies, antibodies to anti-idiotypic antibodies (anti-anti-Id antibody) that can be labeled in soluble or bound form, as well as fragments thereof provided by any known technique, such as, but not limited to enzymatic cleavage, peptide synthesis or recombinant techniques.

A monoclonal antibody contains a substantially homogeneous population of antibodies specific to antigens, which population contains substantially similar epitope binding sites. mAbs may be obtained by methods known to those skilled in the art. See, for example Kohler and Milstein, Nature, 256: 495-497 (1975); U.S. Pat. No.

A monoclonal antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody, which antigen is additionally capable of inducing an animal to produce antibody capable of binding to an epitope of that antigen. An antigen may have one or more than one epitope. The specific reaction referred to above is meant to indicate that the antigen will react, in a highly selective manner, with an epitope on its corresponding antibody and not with the multitude of other antibodies which may be evoked by other antigens.

U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996). Such antibodies may be of any immunoglobulin class including IgG, IgM, An anti-idiotypic (anti-id) antibody is an antibody, which recognizes unique determinants generally associated with the antigen-binding site of an antibody. An Id antibody can be prepared by immunizing an animal of the same species and genetic type (e.g. mouse strain) as the source of the mAb to which an anti-Id is being prepared.

The immunized animal will recognize and respond to the idiotypic determinants of the immunizing antibody by producing an antibody to these idiotypic determinants (the anti-Id antibody). See, for example, U.S. Pat. No. 4,699,880.

The anti-Id antibody may also be used as an "immunogen" to induce an immune response in yet another animal, producing a so-called anti-anti-Id antibody. The anti-anti-Id may be epitopically identical to the original mAb, which induced the anti-id. Thus, by using antibodies to the idiotypic determinants of a MAb, it is possible to identify other clones expressing antibodies of identical specificity.

Accordingly, mAbs generated against NIK fragments may be used to induce anti-Id antibodies in suitable animals, such as BALB/c mice. Spleen cells from such immunized mice are used to produce anti-Id hybridomas secreting anti-Id mAbs. Further, the anti-id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope or fragment of NIK.

The anti-Id mAbs thus have their own idiotypic epitopes, or "idiotopes" structurally similar to the epitope being evaluated.

A preparation of the present invention of a human or humanized antibody or antibody fragment may be preferable for applications involving administration of the preparation to an individual. For example, a human or humanized antibody or antibody fragment will generally tend to be optimally tolerated immunologically, and hence will display an optimal half-life in-vivo in a human, and will thereby display optimal effectiveness. Further guidance regarding production and exploitation of human or humanized antibodies is provided hereinbelow.

The antibodies, including fragments of antibodies, useful in the present invention may be used to quantitatively or qualitatively detect the NIK or a mutein, functional derivative, active fraction, circularly permutated derivative, salt or a portion thereof in a sample or to detect presence of cells that express NIK or a mutein, functional derivative, active fraction, circularly permutated derivative, salt or portions thereof. This can be accomplished by immunofluorescence techniques employing a fluorescently labeled antibody coupled with fluorescence microscopy, flow cytometric, or fluorometric detection.

The antibodies (or fragments thereof) of the present invention may be employed histologically, as in immunofluorescence or immunoelectron microscopy, for in situ detection of NIK or portions thereof of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of NIK or portions thereof but also its distribution on the examined tissue. Using the present invention, those of ordinary skill will readily perceive that any of wide variety of histological methods (such as staining procedures) can be modified in order to achieve such in situ detection.

The biological sample may be coupled to a solid phase support or carrier such as nitrocellulose, or other solid support or carrier which is capable of immobilizing cells, cell particles or soluble proteins. The support or carrier may then be washed with suitable buffers followed by treatment with a labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as 152E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminiescent reaction. The presence of a bioluminescent protein is determined by detecting the presence of luminescence. Important bioluminescent compounds for purposes of labeling are luciferin, luciferase and aequorin.

An antibody preparation of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined, as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The preparation may be used per se or it can be formulated as an active ingredient in a pharmaceutical composition.

Thus, according to the present invention there is provided a pharmaceutical composition comprising a pharmaceutically acceptable carrier and, as an active ingredient, the antibody or antibody fragment of the present invention.

Methods of formulating the antibody or antibody fragment of the present invention as an active ingredient in a pharmaceutical composition, and methods of exploiting such a pharmaceutical composition are described hereinbelow.

As described hereinabove, by virtue of its capacity to specifically bind a region, such as a functional region, of NIK, the antibody or antibody fragment of the present invention can be used for regulating a biochemical activity of a NIK molecule associated with such a functional region.

Thus, according to yet another aspect of the present invention there is provided a method of regulating a biochemical activity of a NIK molecule. The method is effected by contacting the NIK molecule with an antibody or antibody fragment of the present invention.

Preferably, the method is used for regulating the biochemical activity in a human NIK molecule.

Also, the invention relates to the use of a preparation of an antibody or antibody fragment being capable of specifically binding an amino acid sequence, or a portion of said amino acid sequence, said amino acid sequence being set forth in SEQ ID NO: 1, 2, 3, 4, 5, 6, 13, 15, 18, 19, 20, and/or 22 in the manufacture of a medicament for the treatment of a disease caused or aggravated by the activity of NIK.

Another aspect of the invention relates to a method of treatment of a disease caused or aggravated by the activity of NIK which comprise the administration of a preparation of an antibody or antibody fragment being capable of specifically binding an amino acid sequence, or a portion of said amino acid sequence, said amino acid sequence being set forth in SEQ ID NO: 1, 2, 3, 4, 5, 6, 13, 15, 18, 19, 20, and/or 22 to an individual in need.

As described hereinabove, since the antibody or antibody fragment of the present invention is capable of specifically binding the kinase region of NIK in such a way as to down-regulate NIK kinase activity, and since such activity is required for activation of NF-κB, as extensively elaborated in the "Field and Background of the Invention" section above, the method can be used for optimally down-regulating NF-κB activity.

Hence, by virtue of enabling optimal down-regulation of NF-κB activity, the method can be used for optimally treating in an individual a disease associated with disregulated NF-κB activity, in particular excessive or constitutive NF-κB activity.

When using the method according to this aspect of the present invention for treating the disease in the individual, contacting the NIK molecule with the antibody or antibody fragment may be advantageously effected by administering the antibody or antibody fragment to an individual.

Preferably, administering the antibody or antibody fragment is effected by administering the pharmaceutical composition of the present invention comprising the antibody or antibody fragment of the present invention as an active ingredient.

The antibody or antibody fragment is preferably administered so as to achieve a sufficient level of antibody fragment bound to the target antigen so as to achieve a desired regulation of the biochemical activity.

Also, a method for preparing a monoclonal antibody according to the invention is provided. The method comprise growing a cloned hybridoma comprising a spleen cell from a mammal immunized with an amino acid sequence, or a portion of said amino acid sequence, said amino acid sequence is being set forth in SEQ ID NO: 1, 2, 3, 4, 5, 6, 7, 8, 9, 10, 11, 12, 13, 15, 18, 19, 20, or 22, and a homogeneic or heterogeneic lymphoid cell in liquid medium or mammalian abdomen to allow the hybridoma to produce and accumulate the monoclonal antibody.

Example of hybridomas to be used for the preparation of the monoclonal antibodies are the hybridoma clones Pep 7-81.1, Pep 11-355.8, PeP 12-629-62-18 deposited at the CNCM under No. I-3092, No. I-3093 and under No. I-3094 respectively.

An ordinarily skilled artisan, such as a physician, more preferably a physician specialized in the disease, will possess the required expertise for determining a suitable therapeutic protocol, including a suitable route of administration, and a suitable dosage of the antibody or antibody fragment for effectively treating the disease according to the teachings of the present invention.

NIK is normally an intracellular molecule, and, as such, in order to optimally contact the antibody or antibody fragment with the NIK molecule in a cell, such as a cell characterized by disregulated NF-κB activity, the method is preferably practiced in such a way as to facilitate contact of the antibody or antibody fragment with the NIK molecule within the cell.

Such intracellular contacting may be facilitated in various ways, depending on the application and purpose.

For example, such intracellular contacting may be effected by contacting the cell with the antibody or antibody fragment in association with a lipid-based carrier capable of facilitating penetration of the antibody or antibody fragment inside the cell.

Alternatively, such intracellular contacting may be effected by genetically transforming the cell with an expression vector capable of expressing the antibody fragment of the present invention intracellularly.

Suitable types of lipid carriers for facilitating entry of the antibody or antibody fragment into the cell include liposomes, and immunoliposomes. Immunoliposomes, by virtue of enabling cell-type specific delivery of molecules may be advantageously employed for selectively delivering the antibody or antibody fragment in cells affected by disease, where such cells express distinctive surface antigens, such as markers of inflammation in cells displaying a pathological immune response (for example, CD25 or CD69 in activated T lymphocytes), or tumor-associated antigens in malignant cells (for example, HER-2 in adenocarcinoma cells, MAGE-1 in melanoma cells, and the like).

Ample guidance for using such lipid-based carriers for intracellular delivery of therapeutic molecules, such as an antibody or antibody fragment of the present invention, to diseased cells is provided in the literature of the art (for example, refer to: Abra R M. et al., 2002. J Liposome Res. 12:1-3; Park J W., 2002. Breast Cancer Res.; 4(3):95-9; Bendas G., 2001. BioDrugs 15:215-24; Maruyama K., 2000. Biol Pharm Bull. 23:791-9; Hong K. et al., 1999. Ann N.Y. Acad Sci. 886:293-6; Margalit R., 1995. Crit Rev Ther Drug Carrier Syst. 12:233-61; Storm G. and Crommelin D J., 1997. Hybridoma 16:119-25; Park J W. et al., 1997. Adv Pharmacol. 40:399-435).

Producing a recombinant antibody fragment, such as the recombinant antibody fragment of the present invention, intracellularly is routinely practiced in the art. A recombinant antibody fragment expressed intracellularly may be referred to as an "intrabody" in the art. Ample guidance for using intracellular expression of a recombinant antibody fragment capable of specifically binding a biomolecule for regulating a biochemical activity, such as an enzymatic activity, of the biomolecule in a cell is provided in the literature of the art (for example, refer to: Mhashilkar A M. et al., 2002. Gene Ther. 9:307-19; Arafat W. et al., 2000. Cancer Gene Ther. 7:1250-6; Cohen P A. et al., 1998. Oncogene 17:2445-56; Hassanzadeh Gh G. et al., 1998. FEBS Lett. 437:81-6; Richardson J H. et al., 1998. Gene Ther. 5:635-44; for general guidance for expressing a recombinant antibody fragment in a cell, refer, for example, to: der Maur A A. et al., 2002. J Biol Chem. 277:45075-85; Zhu Q. et al., 1999. J Immunol Methods. 231:207-22; Wirtz P. and Steipe B., 1999. Protein Sci. 8:2245-50; Ohage E. and Steipe B., 1999. J Mol Biol. 291: 1119-28).

Genetically transforming a mammalian cell with an expression vector may be effected using any of various commonly practiced art methods, such as stable or transient transfection, lipofection, electroporation and infection with recombinant viral vectors. Ample guidance for practicing such methods is provided in the literature of the art [for example, refer to: Sambrook et al., infra and associated references; Chang et al. in: "Somatic Gene Therapy", CRC Press, Ann Arbor, Mich. (1995); Vega et al. in: "Gene Targeting", CRC Press, Ann Arbor Mich. (1995); Vectors, A Survey of Molecular Cloning Vectors and Their Uses, Butterworths, Boston Mass. (1988); Gilboa et al., 1986. Biotechniques 4:504-512; for vectors involving the central nervous system refer, for example, to U.S. Pat. No. 4,866,042; for positive-negative selection methods for inducing homologous recombination, refer, for example, to: U.S. Pat. Nos. 5,464,764 and 5,487,992].

Further guidance regarding production and exploitation of expression vectors for expressing an antibody fragment of the present invention in a cell is provided hereinbelow.

As described hereinabove, the method according to this aspect of the present invention can be used for optimally treating a disease associated with disregulated NF-κB activity. NF-κB activity is generally involved in activation of a very broad range of immune responses, including those triggered by: lymphocyte antigen receptors, lymphocyte costimulatory receptors, TNF receptors, interleukin receptors, LMP1, RANK, human Toll receptor, and lipopolysaccharide (LPS). Since such receptors are involved in mediating a very broad range of types of immune responses, the method according to this aspect of the present invention can be used for treating numerous diseases whose pathogenesis is associated with such immune responses. Such diseases include autoimmune diseases, inflammatory diseases, transplantation-related diseases, and allergic diseases. For example NF-κB has been shown to be involved in the pathogenesis of diverse examples of such diseases including allergic diseases such as asthma, autoimmune diseases such as rheumatoid arthritis, inflammatory disease such as inflammatory bowel disease, atherosclerosis, and Alzheimer's disease, and transplantation-related diseases such as graft rejection. Furthermore, disregulated NF-κB signaling has been shown to be associated with various malignant diseases.

As such, the method according to this aspect of the present invention can be used for effectively treating diseases such as autoimmune, inflammatory, transplantation-related, allergic, and malignant diseases.

Specific examples of diseases which can be treated according to this aspect of the present invention are listed hereinbelow.

As described hereinabove, the target antigen, which is a polypeptide, may be obtained in various ways.

Preferably, the target antigen is obtained via standard chemical synthesis methodology.

Alternatively, the target antigen may be obtained by proteolytic cleavage of naturally expressed NIK, or may be obtained via standard recombinant techniques using in-vitro expression systems (for example, refer to Sambrook et al. infra, and associated references).

The target antigen may be chemically synthesized using, for example, standard solid phase techniques. Such techniques include exclusive solid phase synthesis, partial solid phase synthesis methods, fragment condensation, classical solution synthesis. Solid phase polypeptide synthesis procedures are well known in the art [for example, refer to Stewart et al., in "Solid Phase Peptide Synthesis", 2nd ed., Pierce Chemical Company, (1984)].

A synthetic polypeptide can be purified by preparative high performance liquid chromatography procedure, such as described by Creighton T. [Proteins, structures and molecular principles, W. H. Freeman and Co. N.Y. (1983)] and its amino acid sequence may be confirmed via standard amino acid sequencing procedures.

As described hereinabove, the preparation is preferably derived by immunizing a mammal with the target antigen.

Generating the preparation in-vivo may be advantageously effected by repeated injection of the target antigen into a mammal in the presence of adjuvants according to a schedule which boosts production of antibodies in the serum. In cases wherein the target antigen is too small to elicit an adequate immunogenic response (referred to as a "hapten" in the art), the hapten can be coupled to an antigenically neutral carrier such as keyhole limpet hemocyanin (KLH) or serum albumin [e.g., bovine serum albumin (BSA)] carriers (for example, refer to U.S. Pat. Nos. 5,189,178 and 5,239,078). Coupling a hapten to a carrier can be effected using various methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Following in-vivo generation of an antibody, its serum titer in the host mammal can readily be measured using immunoassay procedures which are well known in the art.

As described hereinabove, the preparation may advantageously comprise a humanized antibody or antibody fragment.

Chimeric antibodies and methods for their production are known in the art (Cabilly et al., European Patent Application 125023 (published Nov. 14, 1984); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Robinson et al., International Patent Application No. WO 8702671 (published May 7, 1987); Riechmann et al. and Harlow and Lane, ANTIBODIES: A LABORATORY MANUAL, supra.

"Human antibodies" are molecules containing both the variable and constant region of the human immunoglobulin. Fully human antibodies are particularly suitable for therapeutic use, since anti-idiotypic immunogenicity should be significantly reduced or ideally be absent. One method for the preparation of fully human antibodies consist of "humanization" of the mouse humoral immune system, i.e. production of mouse strains able to produce humanIg (Xenomice), by the introduction of human immunoglobulin(Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully human antibodies and methods for their production are known in the art (Mendez et al (1997); Buggemann et al (1991); Tomizuka et al., (2000) Patent WO98/24893).

As used herein the term "muteins" refers to analogs of NIK, in which one or more of the amino acid residues of the naturally occurring components of NIK are replaced by different amino acid residues, or are deleted, or one or more amino acid residues are added to the original sequence of NIK, without changing considerably the activity of the resulting products as compared with the original NIK. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an NIK, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12°20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of NIK, such as to have substantially similar, or even better, activity to NIK.

In a preferred embodiment, any such mutein has at least 40% identity or homology with the amino acid sequence of NIK. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1):387-95), for example the programs BESTFIT and GAP, may be used to determine the % identity between two polynucleotides and the % identity and the % homology between two polypeptide sequences. BESTFIT uses the "local homology" algorithm of Smith and Waterman (J Theor Biol. 1981 Jul. 21; 9.1(2):379-80 and J Mol Biol. 1981 Mar. 25; 147(1):195-7. 1981) and finds the best single region of similarity between two sequences. Other programs for determining identity and/or similarity between sequences are also known in the art, for instance the BLAST family of programs (Altschul S F et al, 1990 J Mol Biol. 1990 Oct. 5; 215(3):403-10, Proc Natl Acad Sci USA. 1990 July; 87(14):5509-13, Altschul S F et al, Nucleic Acids Res. 1997 Sep. 1; 25(17):3389-402, accessible through the home page of the NCBI at www.ncbi.nlm.nih.gov) and FASTA (Pearson W R, Methods Enzymol. 1990; 183:63-98. Pearson J Mol Biol. 1998 Feb. 13; 276(1):71-84).

Muteins of NIK, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of NIK may include synonymous amino acids within a group which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of NIK, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

"Functional derivatives" as used herein cover derivatives of NIK, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of NIK, and do not confer toxic properties on compositions containing it.

An "active fraction" according to the present invention may e.g. be a fragment of NIK. The term fragment refers to any subset of the molecule, that is, a shorter peptide that retains the desired biological activity. Fragments may readily be prepared by removing amino acids from either end of NIK molecule and testing the resultant fragment for its activity. Proteases for removing one amino acid at a time from either the N-terminal or the C-terminal of a polypeptide are known, and so determining fragments, which retain the desired biological activity, involves only routine experimentation.

As active fractions of NIK, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to NIK.

The term "salts" herein refers to both salts of carboxyl groups and to acid addition salts of amino groups of NIK molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of NIK.

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Circularly permuted molecules, which may include DNA, RNA and protein, are single-chain molecules, which have their normal termini fused, often with a linker, and contain new termini at another position. See Goldenberg, et al. J. Mol. Biol., 165: 407-413 (1983) and Pan et al. Gene 125: 111-114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

Humanized antibodies or antibody fragments are genetically engineered chimeric antibodies or antibody fragments having-preferably minimal-portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596). Methods for humanizing non human antibodies or antibody fragments are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies. Human antibodies or antibody fragments can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

As described hereinabove, an antibody fragment of the present invention may be advantageously expressed intracellularly e.g. using an expression vector.

A preferred approach for genetically modifying a cell of an individual with an expression vector is using a viral vector. Viral vectors offer several advantages including higher efficiency of transformation, and targeting to, and propagation in, specific cell types. Viral vectors can also be modified with specific receptors or ligands to alter target specificity through specific cell receptors, such as cancer cell receptors. Such targeting capacity can be used for directing expression of an antibody or antibody fragment of the present invention in a cell characterized by disregulated NF-κB activity.

Retroviral vectors represent one class of vectors suitable for use with the present invention. Defective retroviruses are routinely used as vectors for genetically modifying mammalian cells, such as epithelial cells endothelial cells, lymphocytes, myoblasts, hepatocytes and bone marrow cells, to express recombinant proteins. Portions of the retroviral genome can be removed to render the retrovirus replication defective and the replication defective retrovirus can then packaged into virions, which can be used to infect target cells through the use of a helper virus and while employing standard techniques. Ample guidance for generating a retroviral vector capable of expressing a recombinant protein in a mammalian cell is provided in the literature of the art (for example, refer to Miller, A. D., 1990. Blood 76: 271; Sambrook et al., infra and associated references).

Another suitable expression vector may be an adenoviral vector. Adenoviral vectors are extensively studied and routinely used gene transfer vectors. Key advantages of adenoviral vectors include relatively high transduction efficiency of dividing and quiescent cells, natural tropism to a wide range of epithelial tissues and facile production of high titers. The adenovirus DNA is transported to the nucleus, but does not integrate thereinto. Thus the risk of mutagenesis with adenoviral vectors is minimized. Ample guidance for producing and exploiting adenoviral vectors to treat diseases is provided in the literature of the art [for example, refer to: Russel, W. C., 2000. J. Gen. Virol. 81:57-63; for guidance regarding use of adenoviral vectors cancer treatment, refer, for example, to Seth et al., Adenoviral vectors for cancer gene therapy. In: P. Seth (ed.) Adenoviruses: Basic biology to Gene Therapy, Landes, Austin, Tex., pp. 103-120 (1999)].

A specific example of a suitable adenoviral vector is the adenovirus-derived vector Ad-TK. This vector expresses a herpesvirus thymidine kinase (TK) gene for either positive or negative selection and includes an expression cassette for desired recombinant sequences. This vector can be used to infect cells that have an adenovirus receptor which includes most cancers of epithelial origin (Sandmair et al., 2000. Hum. Gene. Ther. 11:2197-2205).

A suitable viral expression vector may also be a chimeric adenovirus/retrovirus vector which combines retroviral and adenoviral components, and which has been shown to be more efficient than traditional expression vectors. Ample guidance for producing and exploiting such vectors is provided in the literature of the art (for example, refer to Pan et al., 2002. Cancer Letters 184:179-188).

The expression vector can be administered in various ways. If viral vectors are used the procedure can take advantage of their target specificity and consequently, such vectors may not have to be administered locally at an anatomic site affected by the disease. However, local administration can provide a quicker and more effective treatment. Administration of viral vectors can also be performed by, for example, intravenous or subcutaneous injection into the individual. Following injection, the viral vectors will circulate until they recognize host cells with appropriate target specificity for infection.

As described hereinabove, the present invention provides a pharmaceutical composition comprising the antibody or antibody fragment of the present invention as an active ingredient.

As used herein, the phrase "pharmaceutical composition" refers to a preparation of one or more of the active ingredients described herein with other chemical components such as physiologically suitable carriers and excipients. The purpose of a pharmaceutical composition is to facilitate administration of active ingredients to an organism.

Herein the term "active ingredients" refers to the antibody or antibody fragment of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered active ingredients. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration of the pharmaceutical composition may, for example, include oral, rectal, transmucosal, especially transnasal, intestinal or parenteral delivery, including intramuscular, subcutaneous and intramedullary injection as well as intrathecal, direct intraventricular, intravenous, intraperitoneal, intranasal, or intraocular injection.

Alternately, one may administer the pharmaceutical composition in a local rather than systemic manner, for example, via injection of the pharmaceutical composition directly into a tissue region of the individual.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (antibody or antibody fragment of the present invention) capable of preventing, alleviating or ameliorating symptoms of the disease, or prolong the survival of the individual being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in-vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in-vitro, in cell cultures or experimental animals. The data obtained from these in-vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (for example, refer to Fingl, et al., 1975, in "The Pharmacological Basis of Therapeutics", Ch. 1 p. 1).

Dosage amount and interval may be adjusted individually to provide plasma or brain levels of the active ingredients sufficient to exert a desired therapeutic effect (minimal effective concentration, MEC). The MEC will vary for each preparation, but can be estimated from in-vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the individual being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an antibody or antibody fragment of the invention formulated in a compatible pharmaceutical carrier may also be prepared, placed in an appropriate container, and labeled for treatment of an indicated condition, as if further detailed above.

As described hereinabove, the present invention can be used to treat a disease associated with a pathological immune response.

Examples of such diseases include diseases associated with Type I (immediate or IgE-mediated) hypersensitivity, diseases associated with Type II (antibody-mediated) hypersensitivity, diseases associated with Type IV (T lymphocyte-mediated) hypersensitivity, diseases associated with delayed type hypersensitivity (DTH), autoimmune diseases, and diseases associated with transplantation of a graft.

Further examples of diseases associated with hypersensitivity include, for example, diseases associated with Type III (immune complex-mediated) hypersensitivity, diseases associated with inflammation, diseases associated with infection and diseases associated with idiopathic hypersensitivity.

Examples of Type I hypersensitivity include, but are not limited to, allergic diseases such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Examples of Type II hypersensitivity include, but are not limited to, rheumatoid diseases, rheumatoid autoimmune diseases, rheumatoid arthritis (Krenn V. et al., 2000. Histol Histopathol. 15:791), spondylitis, ankylosing spondylitis (Jan Voswinkel et al, 2001. Arthritis Res. 3:189), systemic diseases, systemic autoimmune diseases, systemic lupus erythematosus (Erikson J. et al., 1998. Immunol Res. 17:49), sclerosis, systemic sclerosis (Renaudineau Y., et al., 1999. Clin Diagn Lab Immunol. 6:156); Chan O T. et al., 1999. Immunol Rev. 169:107), glandular diseases, glandular autoimmune diseases, pancreatic autoimmune diseases, diabetes, Type I diabetes (Zimmet P. 1996. Diabetes Res Clin Pract. 34 Suppl: S125), thyroid diseases, autoimmune thyroid diseases, Graves' disease (Orgiazzi J. 2000. Endocrinol Metab Clin North Am. 29:339), thyroiditis, spontaneous autoimmune thyroiditis (Braley-Mullen H. and Yu S. 2000. J Immunol. 165(12):7262), Hashimoto's thyroiditis (Toyoda N. et al., Nippon Rinsho 1999. 57(8):1810), myxedema, idiopathic myxedema (Mitsuma T. Nippon Rinsho. 1999. 57(8):1759); autoimmune reproductive diseases, ovarian diseases, ovarian autoimmunity (Garza K M. et al. J Reprod Immunol. 1998. 37(2):87), autoimmune anti-sperm infertility (Diekman A B. et al., Am J Reprod Immunol. 2000. 43(3):134), repeated fetal loss (Tincani A. et al., Lupus 1998. 7 Suppl 2:S107-9), neurodegenerative diseases, neurological diseases, neurological autoimmune diseases, multiple sclerosis (Cross A H. et al., J Neuroimmunol. 2001. 112(1-2):1), Alzheimer's disease (Oron L. et al., J Neural Transm Suppl. 1997. 49:77), myasthenia gravis (Infante A J. and Kraig E. Int Rev Immunol. 1999. 18(1-2):83), motor neuropathies (Kornberg A J. J Clin Neurosci. 2000. 7(3):191), Guillain-Barre syndrome, neuropathies and autoimmune neuropathies (Kusunoki S. Am J Med Sci. 2000. 319(4):234), myasthenic diseases, Lambert-Eaton myasthenic syndrome (Takamori M. Am J Med Sci. 2000. 319(4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000. 156(1):23); neuropathies, dysimmune neuropathies (Nobile-Orazio E. et al., Electroencephalogr Clin Neurophysiol Suppl. 1999. 50:419); neuromyotonia, acquired neuromyotonia, arthrogryposis multiplex congenita (Vincent A. et al., Ann N.Y. Acad Sci. 1998. 841:482), cardiovascular diseases, cardiovascular autoimmune diseases, atherosclerosis (Matsuura E. et al., Lupus. 1998. 7 Suppl 2:S135), myocardial infarction (Vaarala O. Lupus. 1998. 7 Suppl 2:S132), thrombosis (Tincani A. et al., Lupus 1998. 7 Suppl 2:S107-9), granulomatosis, Wegener's granulomatosis, arteritis, Takayasu's arteritis and Kawasaki syndrome (Praprotnik S. et al., Wien Klin Wochenschr 2000. 112 (15-16):660); anti-factor VIII autoimmune disease (Lacroix-Desmazes S. et al., Semin Thromb Hemost. 2000. 26(2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000. 151(3):178); antiphospholipid syndrome (Flamholz R. et. al., J Clin Apheresis 1999. 14(4): 171); heart failure, agonist-like β-adrenoceptor antibodies in heart failure (Wallukat G. et al., Am J Cardiol. 1999. 83(12A): 75H), thrombocytopenic purpura (Moccia F. Ann Ital Med Int. 1999. 14(2):114); hemolytic anemia, autoimmune hemolytic anemia (Efremov D G. et al., Leuk Lymphoma 1998. 28(34):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000. 138 (2):122), autoimmune diseases of the musculature, myositis, autoimmune myositis, Sjogren's syndrome (Feist E. et al., Int Arch Allergy Immunol. 2000. 123(1):92); smooth muscle autoimmune disease (Zauli D. et al., Biomed Pharnacother. 1999. 53(5-6):234), hepatic diseases, hepatic autoimmune diseases, autoimmune hepatitis (Manns M P. J Hepatol. 2000. 33(2):326) and primary biliary cirrhosis (Strassburg C P. et al., Eur J Gastroenterol Hepatol. 1999. 11(6):595).

Examples of Type III hypersensitivity include, but are not limited to, diseases mediated by immune effector cells such as, for example, neutrophils or macrophages activated by, for example, immune complexes via Fc receptors, such as, for example Fcγ receptors.

Examples of Type IV hypersensitivity include, but are not limited to, rheumatoid diseases, rheumatoid arthritis (Tisch R and McDevitt H O. Proc Natl Acad Sci USA 1994. 91(2): 437), systemic diseases, systemic autoimmune diseases, systemic lupus erythematosus (Datta S K., Lupus 1998. 7(9): 591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol. 1993. 92(1):77); ovarian diseases (Garza K M. et al., J Reprod Immunol. 1998. 37(2):87), prostatitis, autoimmune prostatitis (Alexander R B. et al., Urology 1997. 50(6):893), polyglandular syndrome, autoimmune polyglandular syndrome, Type I autoimmune polyglandular syndrome (Hara T. et al., Blood 1991. 77 (5): 1127), neurological diseases, autoimmune neurological diseases, multiple sclerosis, neuritis, optic neuritis (Soderstrom M. et al., J Neurol Neurosurg Psychiatry 1994. 57(5):544), myasthenia gravis (Oshima M. el al., Eur J Immunol. 1990. 20(12):2563), stiff-man syndrome (Hiemstra H S. et al., Proc Natl Acad Sci USA 2001. 98 (7):3988), cardiovascular diseases, cardiac autoimmunity in Chagas' disease (Cunha-Neto E. et al., J Clin Invest. 1996. 98(8):1709), autoimmune thrombocytopenic purpura (Semple J W. et al., Blood 1996. 87(10):4245), anti-helper T lymphocyte autoimmunity (Caporossi A P. et al., Viral Immunol. 1998. 11(1):9), hemolytic anemia (Sallah S. et al., Ann Hematol. 1997. 74(3):139), hepatic diseases, hepatic autoimmune diseases, hepatitis, chronic active hepatitis (Franco A. et al., Clin Immunol Immunopathol. 1990. 54(3):382), biliary cirrhosis, primary biliary cirrhosis (Jones D E. Clin Sci (Colch) 1996. 91(5):551), nephric diseases, nephric autoimmune diseases, nephritis, interstitial nephritis (Kelly C J. J Am Soc Nephrol. 1990. 1(2):140), connective tissue diseases, ear diseases, autoimmune connective tissue diseases, autoimmune ear disease (Yoo T J. et al., Cell Immunol. 1994. 157 (1):249), disease of the inner ear (Gloddek B. et al., Ann N.Y. Acad Sci. 1997. 830:266), skin diseases, cutaneous diseases, dermal diseases, bullous skin diseases, pemphigus vulgaris, bullous pemphigoid and pemphigus foliaceus.

Examples of diseases associated with delayed type hypersensitivity include, but are not limited to, contact dermatitis and drug eruption.

Examples of autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998 7 Suppl 2:S135), myocardial infarction (Vaarala O. Lupus. 1998. 7 Suppl 2:S132), thrombosis (Tincani A. et al., Lupus 1998. 7 Suppl 2:S107-9), Wegener's granulomatosis, Takayasu's arteritis, Kawasaki syndrome (Praprotnik S. et al., Wien Klin Wochenschr. 2000. 112(15-16):660), anti-factor VIII autoimmune disease (Lacroix-Desmazes S. et al., Semin Thromb Hemost. 2000. 26(2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000. 151(3):178), antiphospholipid syndrome (Flamholz R. et al., J Clin Apheresis 1999. 14(4):171), antibody-induced heart failure (Wallukat G. et al., (1999) Am J Cardiol. 83(12A):75H), thrombocytopenic purpura (Moccia F. Ann Ital Med Int. 1999. 14(2):114; Semple J W. et al., Blood 1996. 87(10):4245), autoimmune hemolytic anemia (Efremov D G. et al., Leuk Lymphoma 1998 28(3-4):285; Sallah S. et al., Ann Hematol. 1997. 74(3):139), cardiac autoimmunity in Chagas' disease (Cunha-Neto E. et al., J Clin Invest. 1996. 98(8):1709) and anti-helper T lymphocyte autoimmunity (Caporossi A P. et al., Viral Immunol. 1998. 11(1):9).

Examples of autoimmune rheumatoid diseases include, but are not limited to rheumatoid arthritis (Krenn V. et al., (2000) Histol Histopathol. 15(3):791; Tisch R, McDevitt H O. (1994) Proc Natl Acad Sci USA. 91(2):437) and ankylosing spondylitis (Jan Voswinkel et al., (2001) Arthritis Res. 3(3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome diseases include, but are not limited to autoimmune diseases of the pancreas, Type 1 diabetes (Castano L. and Eisenbarth G S. 1990. Ann. Rev. Immunol. 8:647; Zimmet P. Diabetes Res Clin Pract. 1996. 34 Suppl: S125), autoimmune thyroid diseases, Graves' disease (Orgiazzi J. Endocrinol Metab Clin North Am. 2000. 29(2):339; Sakata S. et al., Mol Cell Endocrinol. 1993. 92(1):77), spontaneous autoimmune thyroiditis (Braley-Mullen H. and Yu S, J Immunol. 2000. 165(12):7262), Hashimoto's thyroiditis (Toyoda N. et al., Nippon Rinsho 1999. 57(8): 1810), idiopathic myxedema (Mitsuma T. Nippon Rinsho. 1999. 57(8): 1759), ovarian autoimmunity (Garza K M. et al., J Reprod Immunol. 1998. 37(2):87), autoimmune anti-sperm infertility (Diekman A B. et al., Am J Reprod Immunol. 2000. 43(3): 134), autoimmune prostatitis (Alexander R B. et al., Urology 1997, 50(6):893) and Type I autoimmune polyglandular syndrome (Hara T. et al., Blood. 1991. 77 (5):1127).

Examples of autoimmune gastrointestinal diseases include, but are not limited to, chronic inflammatory intestinal diseases (Garcia Herola A. et al., Gastroenterol Hepatol. 2000. 23(1):16), celiac disease (Landau Y E. and Shoenfeld Y. Harefuah 2000. 138(2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol. 1990. 54(3): 382), primary biliary cirrhosis (Jones D E. Clin Sci (Colch) 1996. 91(5):551; Strassburg. C P. et al., Eur J Gastroenterol Hepatol. 1999. 11(6):595) and autoimmune hepatitis (Manns M P. J Hepatol. 2000. 33(2):326).

Examples of autoimmune neurological diseases include, but are not limited to, multiple sclerosis (Cross A H. et al., J Neuroimmunol. 2001. 112(1-2):1), Alzheimer's disease (Oron L. et al., J Neural Transm Suppl. 1997. 49:77), myasthenia gravis (Infante A J. and Kraig E, Int Rev Immunol. 1999. 18(1-2):83; Oshima M. et al., Eur J Immunol. 1990. 20:2563), neuropathies, motor neuropathies Kornberg A J. J Clin Neurosci. 2000. 7:191); Guillain-Barre syndrome and autoimmune neuropathies (Kusunoki S. Am J Med Sci. 2000. 319(4):234), myasthenia, Lambert-Eaton myasthenic syndrome (Takamori M. Am J Med Sci. 2000. 319(4):204); paraneoplastic neurological diseases, cerebellar atrophy, paraneoplastic cerebellar atrophy and stiff-man syndrome (Hiemstra H S. et al., Proc Natl Acad Sci USA 2001. 98(7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol. (Paris) 2000. 156(1):23); dysimmune neuropathies (Nobile-Orazio E. et al., Electroencephalogr Clin Neurophysiol Suppl. 1999. 50:419); acquired neuromyotonia, arthrogryposis multiplex congenita (Vincent A. et al., Ann N.Y. Acad Sci. 1998. 841: 482), neuritis, optic neuritis (Soderstrom M. et al., J Neurol Neurosurg Psychiatry 1994. 57(5):544) and neurodegenerative diseases.

Examples of autoimmune muscular diseases include, but are not limited to, myositis, autoimmune myositis and primary Sjogren's syndrome (Feist E. et al., Int Arch Allergy Immunol. 2000. 123(1):92) and smooth muscle autoimmune disease (Zauli D. et al., Biomed Pharmacother. 1999. 53(5-6):234).

Examples of autoimmune nephric diseases include, but are not limited to, nephritis and autoimmune interstitial nephritis (Kelly C J. J Am Soc Nephrol. 1990. 1(2):140).

Examples of autoimmune diseases related to reproduction include, but are not limited to, repeated fetal loss (Tincani A. et al., Lupus 1998. 7 Suppl 2:S 107-9).

Examples of autoimmune connective tissue diseases include, but are not limited to, ear diseases, autoimmune ear diseases (Yoo T J. et al., Cell Immunol. 1994. 157(1):249) and autoimmune diseases of the inner ear (Gloddek B. et al., Ann N.Y. Acad Sci. 1997. 830:266).

Examples of autoimmune systemic diseases include, but are not limited to, systemic lupus erythematosus (Erikson J. et al., Immunol Res. 1998. 17(1-2):49) and systemic sclerosis (Renaudineau Y. et al., Clin Diagn Lab Immunol. 1999. 6(2): 156); Chan O T. et al., Immunol Rev. 1999. 16:107).

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Examples of transplantation-related diseases include, but are not limited to, graft rejection, chronic graft rejection, subacute graft rejection, hyperacute graft rejection, acute graft rejection and graft-versus-host disease.

Examples of grafts include syngeneic grafts, allografts, xenografts, cellular grafts, tissue grafts, organ grafts and appendage grafts.

Examples of cellular grafts include, but are not limited to, stem cell grafts, progenitor cell grafts, hematopoietic cell grafts, embryonic cell grafts and a nerve cell grafts.

Examples of tissue grafts include, but are not limited to, skin grafts, bone grafts, nerve grafts, intestine grafts, corneal grafts, cartilage grafts, cardiac tissue grafts, cardiac valve grafts, dental grafts, hair follicle grafts and muscle grafts.

Examples of organ grafts include, but are not limited to, kidney grafts, heart grafts, skin grafts, liver grafts, pancreatic grafts, lung grafts and intestine grafts.

Examples of appendage grafts include, but are not limited to, arm grafts, leg grafts, hand grafts, foot grafts, finger grafts, toe grafts and sexual organ grafts.

Examples of inflammatory diseases include, but are not limited to; injuries, neurodegenerative diseases, ulcers, inflammation associated with prosthetic implants, menstruation, septic shock, anaphylactic shock, toxic shock syndrome, cachexia, necrosis, gangrene, musculo-skeletal inflammation and idiopathic inflammation.

Examples of prosthetic implants include, but are not limited to, breast implants, silicone implants, dental implants, penile implants, cardiac implants, artificial joints, bone fracture repair devices, bone replacement implants, drug delivery implants, catheters, pacemakers, respirator tubes and stents.

Examples of ulcers include, but are not limited to, skin ulcers, bed sores, gastric ulcers, peptic ulcers, buccal ulcers, nasopharyngeal ulcers, esophageal ulcers, duodenal ulcers, ulcerative colitis and gastrointestinal ulcers.

Examples of injuries include, but are not limited to, abrasions, bruises, cuts, puncture wounds, lacerations, impact wounds, concussions, contusions, thermal burns, frostbite, chemical burns, sunburns, dessications, radiation burns, radioactivity burns, smoke inhalation, torn muscles, pulled muscles, torn tendons, pulled tendons, pulled ligaments, torn ligaments, hyperextensions, torn cartilage, bone fractures, pinched nerves and a gunshot wounds.

Examples of musculo-skeletal inflammations include, but are not limited to, muscle inflammations, myositis, tendon inflammations, tendinitis, ligament inflammations, cartilage inflammation, joint inflammations, synovial inflammations, carpal tunnel syndrome and bone inflammations.

As used herein the term "about" refers to ±10 percent.

It is expected that during the life of this patent many relevant medical diagnostic techniques will be developed and the scope of the term "detecting" when relating to the target antigen is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren el al., (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al., (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Generation of Monoclonal Antibodies Capable of Binding Human NIK with Optimal Affinity/Specificity As described above, no treatment, or no satisfactory treatment, is available for numerous diseases associated with deregulated NF-κB activity, including malignant diseases and diseases associated with pathological immune responses, such as autoimmune, allergic, inflammatory, transplantation-related diseases. Since NIK is a critical activator of NF-κB, one potentially potent strategy for treating such diseases involves identifying antibodies capable of specifically binding NIK, and of thereby preventing or inhibiting activation of NF-κB by NIK. Such antibodies would also have utility as detection reagents enabling characterization of normal and pathological aspects of biological and biochemical processes involving NIK. The prior art, however, has failed to provide antibodies suitable or optimally suitable for such purposes. While reducing the present invention to practice, such antibodies were unexpectedly identified, thereby overcoming the limitations of the prior art, as described below.

Materials and Methods:

Antibody production: Murine anti-NIK immune sera were generated by immunization of SJL mice with NIK-derived peptides, as previously described [Eshhar Z. in: "Hybridoma Technology in the Biosciences and Medicine", Chapter 1, Springer T A. (eds.) Timothy A., Plenum Publishing Corp., New York (1985)].

Each of the non-overlapping set of NIK-derived peptides shown in Table 1 was used to immunize groups of mice. The positioning of the immunizing peptides relative to the domains of the NIK polypeptide, and the complete amino acid sequence of human NIK showing the location of the immunizing peptides are shown in FIGS. 1 and 2, respectively.

TABLE 1

NIK-derived peptides used for immunizations.

| Peptide designation* | Amino acid sequence** | SEQ ID NO: |
|---|---|---|
| 60-76 | DVITKGTAKEGSEAGPA | 1 |
| 86-99 | CENSQEFSPTFSER | 2 |
| 135-150 | KGKRRSKARKKRKKKS | 3 |
| 215-228 | EGLRPALPRSELHK | 4 |
| 363-378 | RGSRSREPSPKTEDNE | 5 |
| 385-398 | KLKPVDYEYREEVH | 6 |
| 405-420 | RLGRGSFGEVHRMEDK | 7 |
| 427-441 | CAVKKVRLEVFRAEEL | 8 |
| 509-523 | RRILHGDVKADNVLL | 9 |
| 605-619 | CLKIASEPPPVREIP | 10 |
| 635-650 | RKEPIHRVSAAELGGK | 11 |

TABLE 1-continued

NIK-derived peptides used for immunizations.

| Peptide designation* | Amino acid sequence** | SEQ ID NO: |
|---|---|---|
| 666-681 | RGEYKEPRHPPPNQAN | 12 |
| 696-712 | RAPGPRPAEETTGRAPK | 13 |
| 720-736 | EPPEPNKSPPLTLSKEE | 14 |
| 752-767 | PARNPSSPERKATVPE*** | 15 |
| 769-783 | ELQQLEIELFLNSLS | 16 |
| 807-822 | DDSEKNPSKASQSSRD | 17 |
| 836-851 | EARSSSWNMVLARGRP | 18 |
| 871-885 | EHLHIREFHRVKVGD | 19 |
| 904-917 | KDGQPVRYDMEVPD | 20 |

*numbers correspond to amino acid coordinates of peptide within NIK sequence.
**peptides were either selected from the NIK sequence having a natural Cys residue at the N-terminus, or, in the case of peptides shown without a Cys residue at the N-terminus, were synthesized with a supplementary Cys residue at the N-terminus and used as such for immunizations.
***This sequence is very hydrophilic and may be difficult to produce.

Production of recombinant human NIK: For expression of recombinant human NIK fused to a myc (myc-NIK) or polyhistidine (His-NIK) affinity tag, $5\times10^6$, or $2\times10^6$ 293-T cells, respectively, were transfected with expression vector PCS3MTNIK encoding Myc tagged NIK (sequence of NIK as in WO9737016) or pcHis-NIK encoding His tagged NIK, respectively. Cells were transfected via the calcium phosphate [$Ca_3(PO_4)_2$] method in 10 cm-diameter culture dish using 20 μg of expression vector DNA. Twenty-four hours following transfection, PCS3MTNIK or pcHis-NIK transfected cells were harvested, pelleted and lysed in 1.5 ml or 1 ml, respectively, of 1% NP-40 protein lysis buffer.

Immunoprecipitation: For immunoprecipitation of recombinant NIK fusion protein from transfectant protein lysate using immune serum, 1.5 μl of immune serum was mixed with 25 μl of protein G-conjugated beads and 50 μl of lysate, and the volume was completed to 750 μl with lysis buffer. The mixture was incubated at 4° C. for 2 hours. Following incubation, the beads were washed three times with lysis buffer, boiled in 30 μl of sample buffer, and microcentrifuged at 15,000 rpm for 2 minutes. The supernatant (immunoprecipitate) was collected and analyzed for the presence of human NIK via 10% SDS-PAGE.

Western immunoblotting analysis: For 20 wells slot blot, multi-screen Biorad, a 180 μl aliquot of lysate from PCS3MTNIK-transfected 293-T cells was analyzed via SDS-PAGE preparative gel. As a positive control, anti-myc antibody was used at 1:1,000 dilution.

ELISA: Lysate from pcHis-NIK-transfected cells was diluted 25-fold dilution in binding buffer, and 50 μl/well was used for coating ELISA plate wells. Detection of coated NIK or BSA coupled peptide was performed using a 1:100 dilution of anti-NIK immune serum, and the assay was developed using HRP-conjugated sheep anti-mouse antibody with ABTS as enzyme substrate. The $OD_{405}$ of the samples was determined after a 20-minute reaction time.

Experimental Results:

The capacity of commercially available anti-NIK antibodies to detect NIK was assessed via immunoprecipitation/Western immunoblotting assays of myc-NIK in protein lysates of PCS3MTNIK transfected 293-T cells. As can be seen in Table 2, none of the commercially available antibodies tested enables optimal detection of recombinant_NIK.

TABLE 2

Capacity of commercial anti-NIK antibodies for detecting NIK.

| Antibody type | Supplier | NIK-derived immunizing peptide | Assay* | Results |
|---|---|---|---|---|
| mouse IgG mAb | Santacruz | 700-947 | WB | NIK undetectable |
| goat polyclonal | Santacruz | "N-terminal" | WB | Weak detection of overexpressed NIK |
| Rabbit polyclonal | Santacruz | 700-947 | IP, WB | Batch to batch variation. Moderate detection of overexpressed NIK |
| Rabbit polyclonal | Prosci Inc. | 931-947 | WB | Batch to batch variation. Moderate detection of overexpressed NIK (+) |
| Rabitt polyclonal | Pharmingen | 931-947 | WB | Batch to batch variation. Moderate detection of overexpressed NIK (++) |

*WB, Western blot; IP, immunoprecipitation

Figure 3:
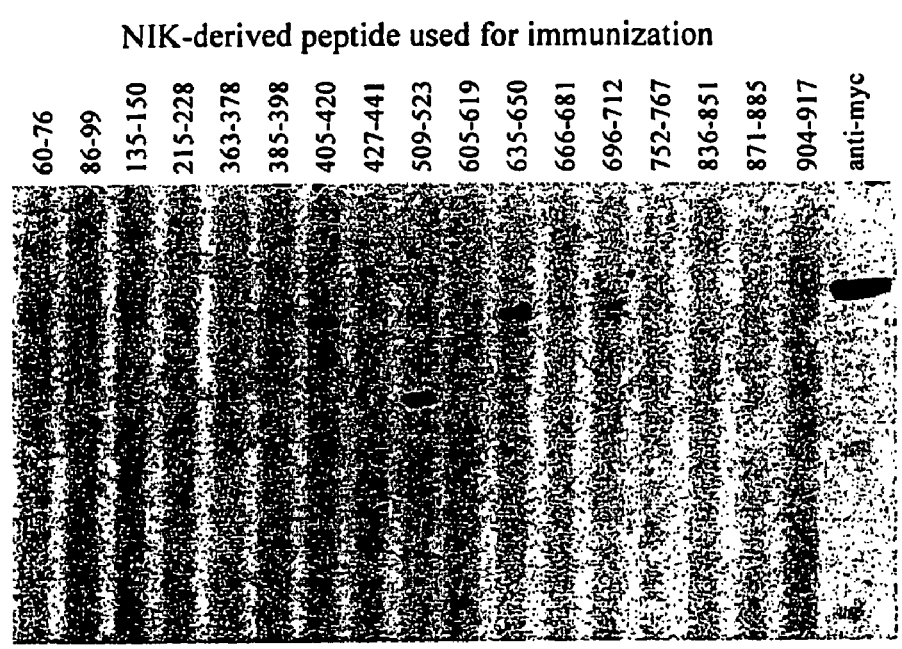
FIG. 3 shows a photograph of a Western immunoblotting analysis depicting the capacity of sera from mice immunized with the indicated NIK-derived peptides to efficiently detect NIK in protein lysate from PCS3MTNIK-transfected cells. Anti-myc-tag antibody was used as a positive control.

The capacity of sera from mice immunized with NIK-derived peptides to detect NIK was analyzed by Western immunoblotting analysis alone or by protein-G-immunoprecipitation of lysate from PCS3MTNIK-transfected cells. As shown in FIG. 3, anti-serum from mice immunized with peptide 405-420, 635-650, 666-681, or 696-712 was found to be capable of effectively detecting NIK by Western immunoblotting analysis. Peptide 405-420 and 635-650, from the amino and carboxy terminal ends of the NIK kinase domain, respectively were found to be very effective for rising excellent antibody for Western immunoblotting analysis. Peptide 666-681 from the carboxy terminal ends of the NIK kinase domain and 696-712 from the C-terminal region respectively were also found to be appropriate for preparing antibodies suitable for Western immunoblotting analysis (FIGS. 1 and 2 and Table 3).

As shown in FIGS. 4a-d, when Myc-NIK was immunoprecipitated with each of the different antibodies prepared from lysates prior to Western immunoblotting analysis (using anti-Myc for detection in Western immunoblotting analysis), anti-sera from mice immunized with peptide 60-76, 86-99, 135-150, or 215-228 (FIG. 4a); 363-378, 385-398, or 405-420 (FIG. 4b); 427-441, 509-523, 605-619, 635-650, 666-681, or 696-712 (FIG. 4c); or 752-767 or 807-822 (FIG. 4d) were each found to have the capacity to immunoprecipitate NIK (shown by the arrow). The capacity of the immune sera to detect NIK was also analyzed by ELISA in a lysate from pcHis-NIK-transfected cells.

Figure 5:
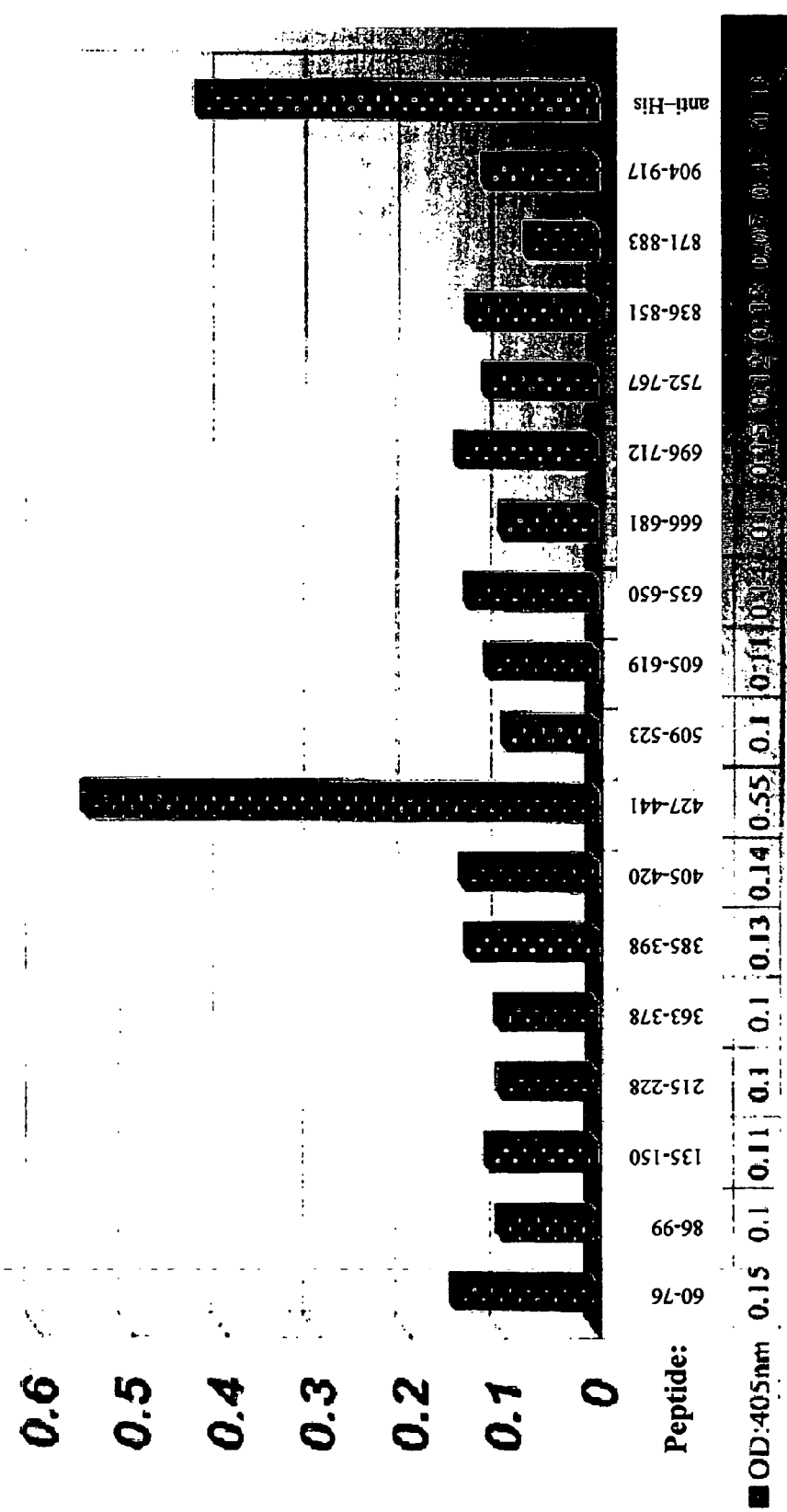
FIG. 5 shows a histogram depicting the capacity of serum from mice immunized with the indicated NIK-derived peptides to detect NIK in protein lysate from pcHis-NIK-transfected cells by ELISA. An anti-His-tag antibody was used as a positive control. Arrows indicate NIK-myc fusion protein.

The antibody prepared using peptides from the C-terminal sub-region of the kinase domain 635-650, or the C-terminal domain of NIK 666-681, 696-712 and 752-767 were found to be extremely efficient for immunoprecipitation of NIK (Table 3). As shown in FIG. 5, serum from mice immunized with peptide 427-441 was found to be capable of detecting NIK with very high sensitivity via ELISA. Serum from mice immunized with peptide 60-76, 86-99, 135-150, 215-228, 363-378, 385-398, 405-420, 509-523, 605-619, 635-650, 666-681, 696-712, 752-767, 836-851 871-883 or 904-917 was also found to be capable of clearly detecting NIK via ELISA.

Thus, as summarized in Table 3, the presently described antibodies have the capacity to efficiently detect human NIK or specific portions thereof via Western immunoblotting analysis, IP/Western immunoblotting assay, and/or ELISA.

Antibody prepared using the C-terminal sub-region of NIK kinase was found to be outstanding in both Western immunoblotting analysis lots and immunoprecipitation of NIK.

Critically, the capacity of the presently described antibodies to specifically bind:

(i) amino acid sequence 60-76 (SEQ ID NO: 1), 86-99 (SEQ ID NO: 2), 135-150 (SEQ ID NO: 3), 215-228 (SEQ ID NO: 4), 363-378 (SEQ ID NO: 5), or 385-398 (SEQ ID NO: 6) of the amino-terminal region of NIK;

(ii) amino acid sequence 401-681 of NIK (SEQ ID NO: 22), which comprises the whole kinase region (amino acid residues 401-681);

(ii) amino acid sequence 405-420 (SEQ ID NO: 7), 427-441 (SEQ ID NO: 8), 509-523 (SEQ ID NO: 9), 605-619 (SEQ ID NO: 10), or 635-650 (SEQ ID NO: 11) of the kinase region of NIK; or (iv) amino acid residues 666-681 (SEQ ID NO: 12), 696-712 (SEQ ID NO: 13), 52-767 (SEQ ID NO: 15), 807-822 (SEQ ID NO: 17), 836-851 (SEQ ID NO: 18), 871-885 (SEQ ID NO: 19), or 904-917 (SEQ ID NO: 20) of the carboxy-terminal region of NIK is unique relative to prior art anti-NIK antibodies (compare Table 2).

TABLE 3

Summary of binding capacities of anti-NIK sera generated.

| origin of immunizing peptide in NIK* | Sub-region | Peptide designation | Detection assay | | |
|---|---|---|---|---|---|
| | | | Western | IP** | ELISA |
| N-terminal region | | 60-76 (SEQ ID NO: 1) | | + | + |
| | | 86-98 (SEQ ID NO: 2) | | + | + |
| | | 135-150 (SEQ ID NO: 3) | | + | + |
| | | 215-228 (SEQ ID NO: 4) | | + | + |
| | | 363-378 (SEQ ID NO: 5) | | + | + |
| | | 385-398 (SEQ ID NO: 6) | | + | + |

TABLE 3-continued

Summary of binding capacities of anti-NIK sera generated.

| origin of immunizing peptide in NIK* | Sub-region | Peptide designation | Detection assay | | |
|---|---|---|---|---|---|
| | | | Western | IP** | ELISA |
| Kinase domain | N-terminal | 405-420 (SEQ ID NO: 7) | +++ | +++ | + |
| | | 427-441 (SEQ ID NO: 8) | | + | +++ |
| | | 509-523 (SEQ ID NO: 9) | | + | + |
| | | 605-619 (SEQ ID NO: 10) | | + | + |
| | C-terminal | 635-650 (SEQ ID NO: 11) | +++ | +++ | + |
| C-terminal region | | 666-681 (SEQ ID NO: 12) | ++ | +++ | + |
| | | 696-712 (SEQ ID NO: 13) | + | +++ | + |
| | | 752-767 (SEQ ID NO: 15) | | +++ | + |
| | | 836-851 (SEQ ID NO: 18) | | + | + |
| | | 871-885 (SEQ ID NO: 19) | | + | + |
| | | 904-917 (SEQ ID NO: 20) | | + | + |

*the N-terminal, kinase, and C-terminal regions of NIK respectively correspond to amino acid residues 1-400, 401-653, and 654-947 of the NIK sequence;
**IP, immunoprecipitation Following extensive experimentation, numerous antibody preparations, each capable of optimally binding a highly specific NIK epitope such as a kinase, amino-terminal, or carboxy-terminal region epitope, were unexpectedly generated. Notably, the capacity of presently described antibody preparations to specifically bind the kinase region of NIK, or to specifically bind any of various specific portions of the kinase, or amino- or carboxy-terminal regions of NIK, is unique relative to all prior art NIK-binding antibodies. Outstanding antibodies being capable of effective detection of NIK in Western immunoblotting analysis where prepared with the N-terminal or C-terminal sub-region of the kinase domain of NIK, or of effective detection of NIK by ELISA were prepared with peptide of the kinase domain 427-441 or of effective detection of NIK by immunoprecipitation were prepared using peptides from the C-terminal domain of NIK including the C-terminal sub-region of the kinase domain (see Table 3). Thus, the presently described antibodies can be used for regulating a biochemical activity, such as a kinase activity, of NIK. Since such activity is required for activation of NF-κB, the presently described antibody preparations can be used for optimally regulating activation of NF-κB, and since deregulation of NF-κB activity is associated with the pathogenesis of numerous diseases, such as those associated with pathological immune responses, and with that of various malignant diseases, the presently described antibody preparations can be used for optimally treating such diseases. Moreover, by virtue of: (i) uniquely and efficiently enabling detection of the kinase region of NIK, or a portion of the kinase region of NIK; and (ii) enabling detection, or optimal detection of NIK, or any of various specific portions of the carboxy- or amino-terminal regions of NIK, the presently described antibody preparations can be exploited for characterizing, or optimally characterizing aspects of normal/pathological biological/biochemical processes/states involving NIK or specific portions thereof.

Preparation of Monoclonal Antibodies

Monoclonal antibodies were prepared as described by Eshhar Z. in: "Hybridoma Technology in the Biosciences and Medicine", Chapter 1, Springer T A. (eds.) Timothy A., Plenum Publishing Corp., New York (1985)] using spleen of the positive mice challenged with peptide of SEQ ID NOs: 7, 11 and 12 of the kinase N and C-terminus for fusion.

Figure 6:
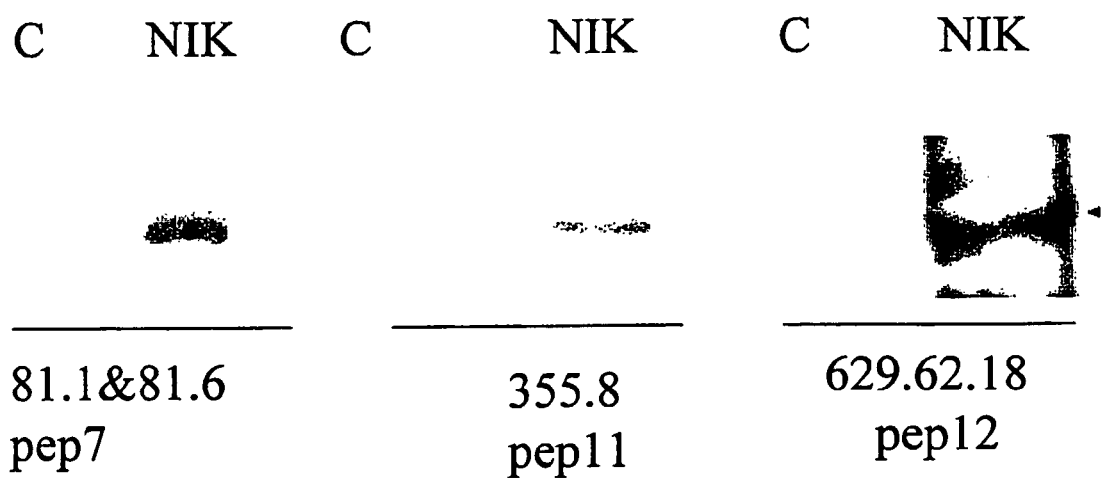
FIG. 6 shows photographs of a Western immunoblotting analysis depicting the capacity of hybridoma supernatant to detect NIK in a protein lysate from PCS3MTNIK-transfected cells. Culture supernatants of three hybridoma Pep 7-81.1, Pep 11-355.8, Pep 12-629-62-18 were tested by Western immunoblotting analysis to detect myc tagged NIK. Western blots were probed with the indicated hybridoma culture supernatant at 1:500 dilution.

Culture supernatants of three hybridomas, developed against peptides of NOs: 7, 11 and 12 of the kinase N and C-terminus (Pep 7 81.1, Pep 11 355.8 and Pep 12 629 62 18), pep 12 is in the beginning of C terminus were tested in Western immunoblotting analysis. Thus, $1.5 \times 10^6$ 293-T cells were seeded on 10 cm plates and transfected after 24 hours with pCS3MTNIK (encoding myc tagged NIK). 24 h post transfection, the cells were harvested and lysed in 1 ml 1% NP40 lysis buffer. 40 μl of the lysate was loaded per lane was loaded on 10% SDS-PAGE along with pcDNA3 transfected cell lysate as a control. Western blots were probed with the respective hybridoma culture supernatant at 1:500 dilution. The results summarized in FIG. 6 show that the monoclonal antibodies, developed against peptides of NOs: 7, 11 and 12 of the kinase N and C-terminus, similarly to the counterpart polyclonal antibodies, are capable of detecting NIK in Western immunoblotting analysis.

293-T lysate expressing myc tagged NIK protein was used also for testing the immunoprecipitating ability of the same three monoclonal anti NIK antibodies: Pep 7 81.1, Pep 11 355.8 and Pep 12 629 62 18. 50 μl of protein G beads was mixed with 500 ul of hybridoma culture supernatant and incubated at about 22° C. for 1 hour. Beads were washed with 1% NP-40 lysis buffer for three times and used for immunoprecipitation. Immunoprecipitation (IP) was carried out for 2 hours at +4° C. After IP, the beads were washed three times and boiled with 50 μl of laemli buffer and 25 μl supernatant was loaded on 10% SDS-PAGE (FIG. 7).

Figure 7:
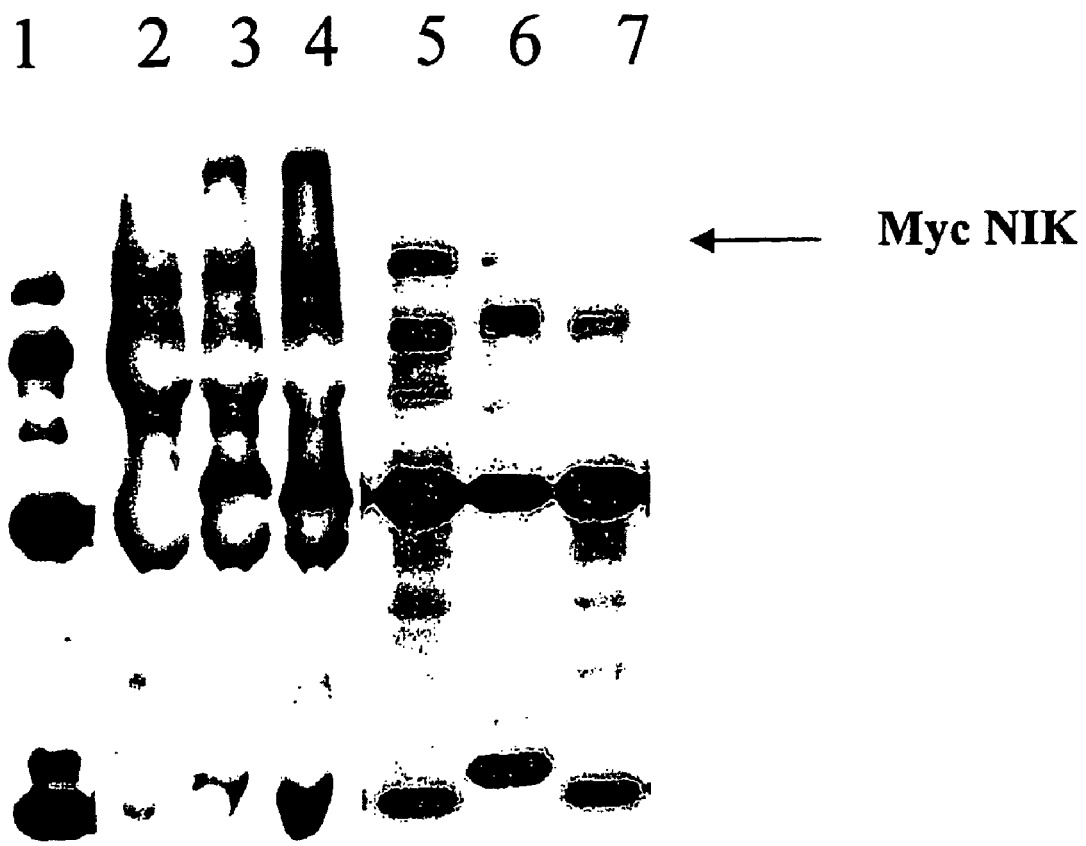
FIG. 7 shows photographs of a Western immunoblotting analysis depicting the capacity of monoclonal antibody Pep 7-81.1, Pep 11-355.8, Pep 12-629-62-18 to detect NIK in protein-G-immunoprecipitated protein lysate from PCS3MTNIK-transfected cells. Immunoprecipitation: 293-T lysate expressing myc tagged NIK protein was used as substrate for testing the immunoprecipitating ability of the indicated monoclonal antibodies. Lane 1: Affinity purified pep7-81 antibody from ascitic fluid. Lane 2. Pep12-629.62.18 antibody lane 3. Pep11 355.8 antibody, lane 4. Pep7 81.1 antibody, lane 5 anti myc, lane 6 pep12 629.62.25 antibody from ascites, lane 7 mouse IgG control.

The results summarized in FIG. 7 show that all the tested monoclonal antibodies were capable of immunoprecipitate NIK, except for the negative control IgG (FIG. 7 line 7). Affinity purified antibody from asciteswere superior than antibody purified from hybridoma supernatants (compare lines 1 and 4 in FIG. 7).

Detection of Endogenous NIK.

To explore the possibility of detecting endogenous NIK, Ramos cells ($2-4 \times 10^8$; $1 \times 10^8$ cells/ml) were lysed and NIK was immunoprecipitated with affinity-purified mouse-NIK ascites, containing purified NIK-81 antibody (i.e. Pep7 81.1 monoclonal antibody) coupled to protein-G-Sepharose beads (coupled as described above). NIK-81 antibody was purified from mouse ascitic fluids on affinity colums, to which the peptide used to prepare the antibody (SEQ ID NO: 7) was coupled.

The antibodies were purified from ascites fluid by affinity purification using affigel beads (affigel 15 Biorad) crosslinked with BSA (Pierce Cat 77116) coupled to the synthetic peptide used for mice immunization (peptide in SEQ ID NO: 7). One ml of affigel 15 was washed with cold double ditilled water, three times, 10 ml each. Washed affigel was mixed with 1 ml of BSA couled peptide at 4 degrees for 12-16 hours in rotator. Blocking of ester was done by adding 100 microlitre of 1M ethanolamine (pH 8.0)/ml gel and incubated for one hour at 4 degrees in rotator.

For antibody purification, ascites precipitated by 50% ammonium sulphate was dialyzed against PBS for 1630 hours hours at 4° C. Following dialysis, aliquots were incubated with 1 ml of processed affigel-BSA-peptide beads for 12-16 hours at 4° C. and the pre-incubated beads were used to pack a 1 ml column. Initially the column was washed with 10 ml PBS, followed by a wash with 10 mM Tris pH 7.5 containing 1 M NaCl and a wash with PBS. The antibodies were eluted from the column with a solution containing 100 mM glycine HCl pH 2.7 and 0.5M NaCl. 1 ml fractions were collected in tubes containing 40 µl Tris base for the neutralization of the eluant. From 25 ml ascites about 5-13.6 mg-purified antibodies was obtained.

Figure 8:
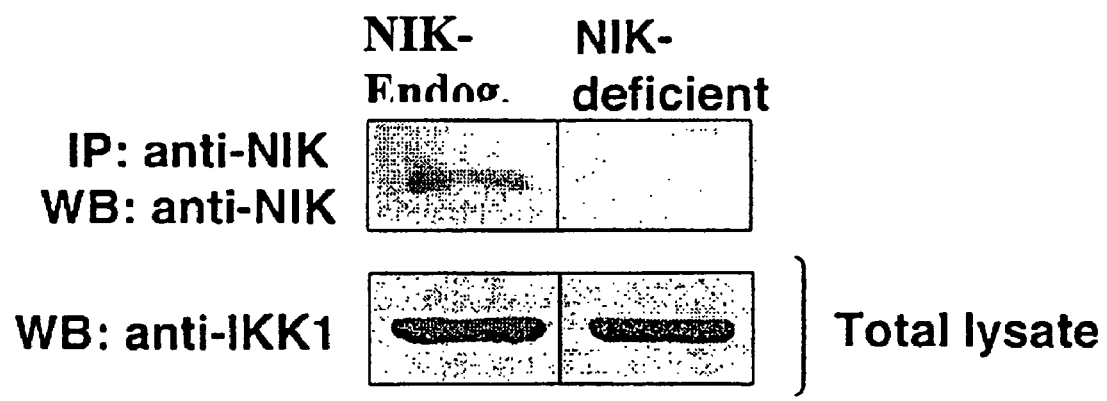
FIG. 8 shows the detection of endogenous NIK in Ramos cells by monoclonal antibody anti NIK 81.

Immunoprecipitated protein was detected by Western blotting analysis using the NIK-81 antibody and SuperSignal West Femto Chemiluminescent Detection Kit (Pierce). NIK (and for comparison, IKK1) was monitored in NIK deficient Ramos cells (expressing constitutively lentiviral pSUPER-NIK) and in Ramos cells containing endogenous NIK (transduced with lentiviral-GFP). The results obtained (FIG. 8) show that NIK-81 antibody is capable of efficient immunoprecipitation of endogenous NIK and detection in Western immunoblotting analysis.

Detection of Murine NIK by NIK-81 Antibody.

Since murine antibodies are valuable tools for in vivo research, particularly in murine models, it was explored whether the monoclonal antibody NIK 81, is capable to detect murine NIK. For that purpose, Hela cells ($1.2 \times 10^6$ cells seeded in 9 cm petriplate) were transfected with 5 mcg plasmid, encoding human (hNIK) or mouse NIK (mNIK), or respective fragments thereof (hNIK 188-947 and mNIK 87-942) or control empty plasmid (pcHIS), by the calcium phosphate precipitation method.

Twenty four hours post transfection, total cell lysates were analysed for transient overexpressed human or mouse NIK by Western immunoblotting analysis with anti NIK 81 antibody (Ascitic fluid 1:5000 dilution).

Figure 9:
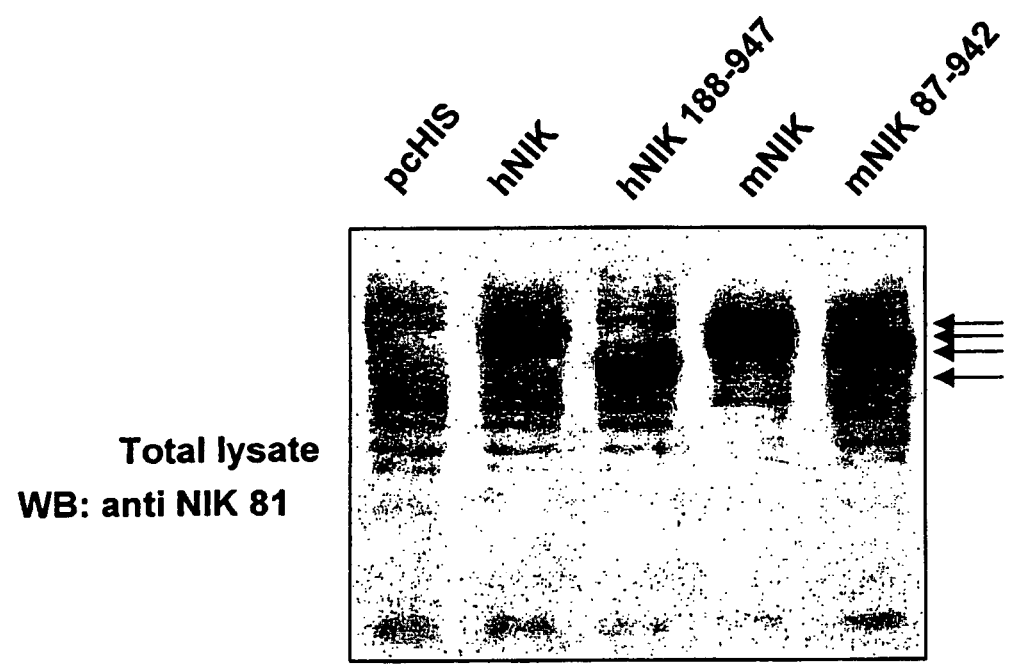
FIG. 9 shows detection of mouse NIK over expressed in Hela cells with monoclonal antibody anti NIK 81.

The results summarized on FIG. 9 show that the monoclonal antibody anti NIK 81 is capable of binding and detecting, human NIK, murine NIK and fragments thereof.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications and sequences identified by their accession numbers mentioned in this specification are herein incorporated in their entirety by reference into the specification, to the same extent as if each individual publication, patent, or patent application or sequence identified by its accession number was specifically and individually indicated to be incorporated herein by reference. In addition, citation or identification of any reference in this application shall not be construed as an admission that such reference is available as prior art to the present invention.

Hybridoma clones Pep 7-81.1, Pep 11-355.8 and PeP 12-629-62-18 were deposited on Oct. 2, 2003 at the Collection Nationale de Culture de Microorganismes (CNCM), Institut Pasteur, Paris, under the Budapest Treaty and were accorded deposit Nos. I-3092, I-3093, I-3094, respectively.

The invention claimed is:

1. A preparation comprising one or more polyclonal, monoclonal, chimeric, humanized, human or anti-anti-idiotype antibodies and/or fragments thereof being capable of specifically binding the amino acid sequence set forth in SEQ ID NO: 7, 11, or 12 and capable of detecting NF-κB inducing kinase (NIK) in a Western blot, enzyme-linked immunosorbent assay (ELISA), or immunoprecipitation assay.

2. The antibody preparation of claim 1, wherein said amino acid sequence is located in a flanking region of the NIK kinase domain.

3. The antibody preparation of claim 1 wherein said amino acid sequence is SEQ ID NO: 7.

4. The antibody preparation of claim 1 wherein said amino acid sequence is SEQ ID NO: 11.

5. The antibody preparation of claim 2 wherein said amino acid sequence is SEQ ID NO: 12.

6. The antibody preparation of claim 1, wherein said antibody is an IgG antibody.

7. The antibody preparation of claim 1, wherein said antibody fragment is selected from the group consisting of a single-chain Fv, an Fab, an Fab', and an F(ab')2.

8. The antibody preparation of claim 1, wherein said antibody or antibody fragment is further capable of regulating a biochemical activity of a NIK molecule.

9. The antibody preparation according to claim 1, capable of specifically detecting NIK by Western immunoblotting analysis.

10. The antibody preparation according to claim 1, capable of specifically detecting NIK by ELISA.

11. The antibody preparation according to claim 1, capable of specifically detecting NIK by immunoprecipitation.

12. A preparation comprising one or more polyclonal, monoclonal, chimeric, humanized, human or anti-anti-idiotype antibodies and/or fragments thereof being capable of specifically binding NIK, the antibody prepared by immunizing a mammal with a peptide comprising the amino acid sequence set forth in SEQ ID NO: 7.

13. A preparation according to claim 12, capable of detecting murine NIK.

14. A preparation according to claim 12, prepared by immunizing a rodent.

15. A method for preparing a monoclonal antibody comprising immunizing a mammal with a peptide consisting essentially of the amino acid sequence set forth in SEQ ID NO: 7, 11, or 12.

16. A monoclonal antibody specifically binding the amino acid sequence set forth in SEQ ID NO: 7, 11, or 12.

17. The monoclonal antibody of claim 16, wherein said amino acid sequence is in the flanking region of the NIK kinase domain.

18. The monoclonal antibody of claim 16, wherein said amino acid sequence is set forth in SEQ ID NO: 7.

19. The monoclonal antibody of claim 16, wherein said amino acid sequence is set forth in SEQ ID NO: 11.

20. The monoclonal antibody of claim 16, wherein said amino acid sequence is set forth in SEQ ID NO: 12.

21. The monoclonal antibody of claim 16 generated by hybridoma clone Pep 7-81.1 deposited at the CNCM under No. I-3092.

22. The monoclonal antibody of claim 16 generated by hybridoma clone Pep 11-355.8 deposited at the CNCM under No. I-3093.

23. The monoclonal antibody of claim 16 generated by hybridoma clone Pep 12-629-62-18 deposited at the CNCM under No. I-3094.

24. A hybridoma clone deposited at the CNCM under No. I-3092.

25. A hybridoma clone deposited at the CNCM under No. I-3093.

26. A hybridoma clone deposited at the CNCM under No. I-3094.

27. A pharmaceutical composition comprising a pharmaceutically acceptable carrier and one or more polyclonal, monoclonal, chimeric, humanized, human or anti-anti-idiotype antibodies and/or fragments thereof capable of specifically binding the amino acid sequence set forth in SEQ ID NO: 7, 11, or 12.

28. The pharmaceutical composition of claim 27, wherein said amino acid sequence is SEQ ID NO: 7.

29. The pharmaceutical composition of claim 27, wherein said amino acid sequence is SEQ ID NO: 11.

30. The pharmaceutical composition of claim 27, wherein said amino acid sequence is SEQ ID NO: 12.

31. The pharmaceutical composition of claim 27, wherein said antibody is an IgG antibody.

32. The pharmaceutical composition of claim 27, wherein said polyclonal, monoclonal, chimeric, humanized or anti-anti-idiotype antibody or antibody fragment is derived from mouse.

33. The pharmaceutical composition of claim 27, wherein said antibody fragment is selected from the group consisting of a single-chain Fv, an Fab, an Fab', and an F(ab')2.

34. The pharmaceutical composition of claim 27, wherein said antibody or antibody fragment is further capable of regulating a biochemical activity of a NIK molecule.

* * * * *

SEQUENCE LISTING

```
<160> NUMBER OF SEQ ID NOS: 22

<210> SEQ ID NO 1
<211> LENGTH: 17
<212> TYPE: PRT
<213> ORGANISM: Artificial sequence
<220> FEATURE:
<223> OTHER INFORMATION: Synthetic peptide

<400> SEQUENCE: 1

Asp Val Ile Thr Lys Gly Thr Ala Lys Glu Gly Ser Glu Ala Gly Pro
1               5                   10                  15

Ala

<210> SEQ ID NO 2
<211> LENGTH: 14
<212> TYPE: PRT
<213> ORGANISM: Artificial sequence
<220> FEATURE:
<223> OTHER INFORMATION: Synthetic peptide

<400> SEQUENCE: 2

Cys Glu Asn Ser Gln Glu Phe Ser Pro Thr Phe Ser Glu Arg
1               5                   10

<210> SEQ ID NO 3
<211> LENGTH: 16
<212> TYPE: PRT
<213> ORGANISM: Artificial sequence
<220> FEATURE:
```

<223> OTHER INFORMATION: Synthetic peptide

<400> SEQUENCE: 3

Lys Gly Lys Arg Arg Ser Lys Ala Arg Lys Lys Arg Lys Lys Ser
1               5                   10                  15

<210> SEQ ID NO 4
<211> LENGTH: 14
<212> TYPE: PRT
<213> ORGANISM: Artificial sequence
<220> FEATURE:
<223> OTHER INFORMATION: Synthetic peptide

<400> SEQUENCE: 4

Glu Gly Leu Arg Pro Ala Leu Pro Arg Ser Glu Leu His Lys
1               5                   10

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Arg Gly Ser Arg Ser Arg Glu Pro Ser Pro Lys Thr Glu Asp Asn Glu
1               5                   10                  15

<210> SEQ ID NO 6
<211> LENGTH: 14
<212> TYPE: PRT
<213> ORGANISM: Artificial sequence
<220> FEATURE:
<223> OTHER INFORMATION: Synthetic peptide

<400> SEQUENCE: 6

Lys Leu Lys Pro Val Asp Tyr Glu Tyr Arg Glu Glu Val His
1               5                   10

<210> SEQ ID NO 7
<211> LENGTH: 16
<212> TYPE: PRT
<213> ORGANISM: Artificial sequence
<220> FEATURE:
<223> OTHER INFORMATION: Synthetic peptide

<400> SEQUENCE: 7

Arg Leu Gly Arg Gly Ser Phe Gly Glu Val His Arg Met Glu Asp Lys
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Synthetic peptide

<400> SEQUENCE: 8

Cys Ala Val Lys Lys Val Arg Leu Glu Val Phe Arg Ala Glu Glu Leu
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic peptide -continued

```
<400> SEQUENCE: 9

Arg Arg Ile Leu His Gly Asp Val Lys Ala Asp Asn Val Leu Leu
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Cys Leu Lys Ile Ala Ser Glu Pro Pro Val Arg Glu Ile Pro
1               5                   10                  15

<210> SEQ ID NO 11
<211> LENGTH: 16
<212> TYPE: PRT
<213> ORGANISM: Artificial sequence
<220> FEATURE:
<223> OTHER INFORMATION: Synthetic peptide

<400> SEQUENCE: 11

Arg Lys Glu Pro Ile His Arg Val Ser Ala Ala Glu Leu Gly Gly Lys
1               5                   10                  15

<210> SEQ ID NO 12
<211> LENGTH: 16
<212> TYPE: PRT
<213> ORGANISM: Artificial sequence
<220> FEATURE:
<223> OTHER INFORMATION: Synthetic peptide

<400> SEQUENCE: 12

Arg Gly Glu Tyr Lys Glu Pro Arg His Pro Pro Asn Gln Ala Asn
1               5                   10                  15

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Arg Ala Pro Gly Pro Arg Pro Ala Glu Glu Thr Thr Gly Arg Ala Pro
1               5                   10                  15

Lys

<210> SEQ ID NO 14
<211> LENGTH: 17
<212> TYPE: PRT
<213> ORGANISM: Artificial sequence
<220> FEATURE:
<223> OTHER INFORMATION: Synthetic peptide

<400> SEQUENCE: 14

Glu Pro Pro Glu Pro Asn Lys Ser Pro Pro Leu Thr Leu Ser Lys Glu
1               5                   10                  15

Glu

<210> SEQ ID NO 15
<211> LENGTH: 16
<212> TYPE: PRT
<213> ORGANISM: Artificial sequence
<220> FEATURE:
```

<223> OTHER INFORMATION: Synthetic peptide

<400> SEQUENCE: 15

Pro Ala Arg Asn Pro Ser Ser Pro Glu Arg Lys Ala Thr Val Pro Glu
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Synthetic peptide

<400> SEQUENCE: 16

Glu Leu Gln Gln Leu Glu Ile Glu Leu Phe Leu Asn Ser Leu Ser
1               5                   10                  15

<210> SEQ ID NO 17
<211> LENGTH: 16
<212> TYPE: PRT
<213> ORGANISM: Artificial sequence
<220> FEATURE:
<223> OTHER INFORMATION: Synthetic peptide

<400> SEQUENCE: 17

Asp Asp Ser Glu Lys Asn Pro Ser Lys Ala Ser Gln Ser Ser Arg Asp
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: Synthetic peptide

<400> SEQUENCE: 18

Glu Ala Arg Ser Ser Ser Trp Asn Met Val Leu Ala Arg Gly Arg Pro
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Synthetic peptide

<400> SEQUENCE: 19

Glu His Leu His Ile Arg Glu Phe His Arg Val Lys Val Gly Asp
1               5                   10                  15

<210> SEQ ID NO 20
<211> LENGTH: 14
<212> TYPE: PRT
<213> ORGANISM: Artificial sequence
<220> FEATURE:
<223> OTHER INFORMATION: Synthetic peptide

<400> SEQUENCE: 20

Lys Asp Gly Gln Pro Val Arg Tyr Asp Met Glu Val Pro Asp
1               5                   10

<210> SEQ ID NO 21
<211> LENGTH: 947
<212> TYPE: PRT
<213> ORGANISM: Artificial sequence
<220> FEATURE:
<223> OTHER INFORMATION: Synthetic peptide

<400> SEQUENCE: 21

```
Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
            20                  25                  30

Gly Lys Lys Gln Ser Ser Val Tyr Lys Leu Glu Ala Val Glu Lys Ser
        35                  40                  45

Pro Val Phe Cys Gly Lys Trp Glu Ile Leu Asn Asp Val Ile Thr Lys
50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

Ser Leu Asp Gln Ile Pro Asn Asn Val Ala His Ala Thr Glu Gly Lys
        115                 120                 125

Met Ala Arg Val Cys Trp Lys Gly Lys Arg Ser Lys Ala Arg Lys
130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175

Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
            260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gln Ala His Ser
            340                 345                 350

Leu Thr Ser Leu Ala Lys Thr Trp Ala Ala Arg Gly Ser Arg Ser Arg
        355                 360                 365

Glu Pro Ser Pro Lys Thr Glu Asp Asn Glu Gly Val Leu Leu Thr Glu
370                 375                 380

Lys Leu Lys Pro Val Asp Tyr Glu Tyr Arg Glu Val His Trp Ala
385                 390                 395                 400

Thr His Gln Leu Arg Leu Gly Arg Gly Ser Phe Gly Glu Val His Arg
                405                 410                 415
```

```
Met Glu Asp Lys Gln Thr Gly Phe Gln Cys Ala Val Lys Lys Val Arg
            420                 425                 430

Leu Glu Val Phe Arg Ala Glu Leu Met Ala Cys Ala Gly Leu Thr
        435                 440                 445

Ser Pro Arg Ile Val Pro Leu Tyr Gly Ala Val Arg Glu Gly Pro Trp
    450                 455                 460

Val Asn Ile Phe Met Glu Leu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
            500                 505                 510

His Gly Asp Val Lys Ala Asp Asn Val Leu Leu Ser Ser Asp Gly Ser
        515                 520                 525

His Ala Ala Leu Cys Asp Phe Gly His Ala Val Cys Leu Gln Pro Asp
    530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
            580                 585                 590

Cys His Pro Trp Thr Gln Phe Phe Arg Gly Pro Leu Cys Leu Lys Ile
        595                 600                 605

Ala Ser Glu Pro Pro Val Arg Glu Ile Pro Pro Ser Cys Ala Pro
    610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                645                 650                 655

Gln Val Gly Gly Leu Lys Ser Pro Trp Arg Gly Glu Tyr Lys Glu Pro
            660                 665                 670

Arg His Pro Pro Asn Gln Ala Asn Tyr His Gln Thr Leu His Ala
        675                 680                 685

Gln Pro Arg Glu Leu Ser Pro Arg Ala Pro Gly Pro Arg Pro Ala Glu
    690                 695                 700

Glu Thr Thr Gly Arg Ala Pro Lys Leu Gln Pro Pro Leu Pro Pro Glu
705                 710                 715                 720

Pro Pro Glu Pro Asn Lys Ser Pro Pro Leu Thr Leu Ser Lys Glu Glu
                725                 730                 735

Ser Gly Met Trp Glu Pro Leu Pro Leu Ser Ser Leu Glu Pro Ala Pro
            740                 745                 750

Ala Arg Asn Pro Ser Ser Pro Glu Arg Lys Ala Thr Val Pro Glu Gln
        755                 760                 765

Glu Leu Gln Gln Leu Glu Ile Glu Leu Phe Leu Asn Ser Leu Ser Gln
    770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Asp Ser Glu Lys Asn Pro Ser Lys Ala
                805                 810                 815

Ser Gln Ser Ser Arg Asp Thr Leu Ser Ser Gly Val His Ser Trp Ser
            820                 825                 830

Ser Gln Ala Glu Ala Arg Ser Ser Ser Trp Asn Met Val Leu Ala Arg
        835                 840                 845
```

Gly Arg Pro Thr Asp Thr Pro Ser Tyr Phe Asn Gly Val Lys Val Gln
    850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                885                 890                 895

Ala Ala Phe Ser Leu Val Thr Lys Asp Gly Gln Pro Val Arg Tyr Asp
                900                 905                 910

Met Glu Val Pro Asp Ser Gly Ile Asp Leu Gln Cys Thr Leu Ala Pro
            915                 920                 925

Asp Gly Ser Phe Ala Trp Ser Trp Arg Val Lys His Gly Gln Leu Glu
930                 935                 940

Asn Arg Pro
945

<210> SEQ ID NO 22
<211> LENGTH: 281
<212> TYPE: PRT
<213> ORGANISM: Artificial sequence
<220> FEATURE:
<223> OTHER INFORMATION: Synthetic peptide

<400> SEQUENCE: 22

Thr His Gln Leu Arg Leu Gly Arg Gly Ser Phe Gly Glu Val His Arg
1               5                   10                  15

Met Glu Asp Lys Gln Thr Gly Phe Gln Cys Ala Val Lys Lys Val Arg
            20                  25                  30

Leu Glu Val Phe Arg Ala Glu Glu Leu Met Ala Cys Ala Gly Leu Thr
        35                  40                  45

Ser Pro Arg Ile Val Pro Leu Tyr Gly Ala Val Arg Glu Gly Pro Trp
    50                  55                  60

Val Asn Ile Phe Met Glu Leu Leu Glu Gly Gly Ser Leu Gly Gln Leu
65                  70                  75                  80

Val Lys Glu Gln Gly Cys Leu Pro Glu Asp Arg Ala Leu Tyr Tyr Leu
                85                  90                  95

Gly Gln Ala Leu Glu Gly Leu Glu Tyr Leu His Ser Arg Arg Ile Leu
            100                 105                 110

His Gly Asp Val Lys Ala Asp Asn Val Leu Leu Ser Ser Asp Gly Ser
        115                 120                 125

His Ala Ala Leu Cys Asp Phe Gly His Ala Val Cys Leu Gln Pro Asp
    130                 135                 140

Gly Leu Gly Lys Ser Leu Leu Thr Gly Asp Tyr Ile Pro Gly Thr Glu
145                 150                 155                 160

Thr His Met Ala Pro Glu Val Val Leu Gly Arg Ser Cys Asp Ala Lys
                165                 170                 175

Val Asp Val Trp Ser Ser Cys Cys Met Met Leu His Met Leu Asn Gly
            180                 185                 190

Cys His Pro Trp Thr Gln Phe Phe Arg Gly Pro Leu Cys Leu Lys Ile
        195                 200                 205

Ala Ser Glu Pro Pro Pro Val Arg Glu Ile Pro Ser Cys Ala Pro
    210                 215                 220

Leu Thr Ala Gln Ala Ile Gln Glu Gly Leu Arg Lys Glu Pro Ile His
225                 230                 235                 240

Arg Val Ser Ala Ala Glu Leu Gly Gly Lys Val Asn Arg Ala Leu Gln
                245                 250                 255

-continued

```
Gln Val Gly Gly Leu Lys Ser Pro Trp Arg Gly Glu Tyr Lys Glu Pro
            260                 265                 270

Arg His Pro Pro Pro Asn Gln Ala Asn
        275                 280
```